(12) United States Patent
Overbeek et al.

(10) Patent No.: US 12,281,072 B2
(45) Date of Patent: *Apr. 22, 2025

(54) MULTI-AZIRIDINE COMPOUND

(71) Applicant: COVESTRO (NETHERLANDS) B.V., Geleen (NL)

(72) Inventors: Gerardus Cornelis Overbeek, Geleen (NL); Patrick Johannes Maria Stals, Geleen (NL); Daan Van Der Zwaag, Geleen (NL); Alfred Jean Paul Bückmann, Geleen (NL); Josephus Christiaan Van Oorschot, Geleen (NL)

(73) Assignee: Covestro (Netherlands) B.V., Geleen (NL)

( * ) Notice: Subject to any disclaimer, the term of this patent is extended or adjusted under 35 U.S.C. 154(b) by 479 days.

This patent is subject to a terminal disclaimer.

(21) Appl. No.: 17/794,440

(22) PCT Filed: Jan. 21, 2021

(86) PCT No.: PCT/EP2021/051392
§ 371 (c)(1),
(2) Date: Jul. 21, 2022

(87) PCT Pub. No.: WO2021/148570
PCT Pub. Date: Jul. 29, 2021

(65) Prior Publication Data
US 2023/0127229 A1    Apr. 27, 2023

(30) Foreign Application Priority Data

Jan. 22, 2020 (EP) .................... 20153154
Jan. 22, 2020 (EP) .................... 20153159
Jan. 22, 2020 (EP) .................... 20153239
Jan. 22, 2020 (EP) .................... 20153240
Jan. 22, 2020 (EP) .................... 20153242
Jan. 22, 2020 (EP) .................... 20153245
Jan. 22, 2020 (EP) .................... 20153246
Jan. 22, 2020 (EP) .................... 20153249
Jan. 22, 2020 (EP) .................... 20153250
Jan. 22, 2020 (EP) .................... 20153251
Jan. 22, 2020 (EP) .................... 20153253
Jan. 24, 2020 (EP) .................... 20153628
Jan. 24, 2020 (EP) .................... 20153630
Jul. 24, 2020 (EP) .................... 20187717

(51) Int. Cl.
*C07D 203/10* (2006.01)
*C07D 251/32* (2006.01)
(Continued)

(52) U.S. Cl.
CPC ......... *C07D 203/10* (2013.01); *C07D 251/32* (2013.01); *C07D 403/12* (2013.01);
(Continued)

(58) Field of Classification Search
CPC .. C07D 203/10; C07D 251/32; C07D 403/12; C07D 403/14; C07D 413/14;
(Continued)

(56) References Cited

U.S. PATENT DOCUMENTS 3,329,674 A   7/1967  Bulbenko et al.
3,337,533 A   8/1967  Ham
(Continued)

FOREIGN PATENT DOCUMENTS

CN   1368524 A   9/2002
CN   1606574 A   4/2005
(Continued)

OTHER PUBLICATIONS

International Search Report for PCT/EP2021/051392 dated Apr. 14, 2021 (3 pages).
(Continued)

*Primary Examiner* — Michael L Leonard
(74) *Attorney, Agent, or Firm* — The Webb Law Firm

(57) ABSTRACT

The present invention relates to a multi-aziridine compound having: a) at least 2 of the following structural units (A): (A) whereby $R_1$ is H; $R_2$ and $R_4$ are independently chosen from H, a linear group containing from 1 to 8 carbon atoms and optionally containing one or more heteroatoms, a branched or cyclic group containing from 3 to 8 carbon atoms and optionally containing one or more heteroatoms, phenyl, benzyl, or pyridinyl; $R_3$ is chosen from a linear group containing from 1 to 8 carbon atoms and optionally containing one or more heteroatoms, a branched or cyclic group containing from 3 to 8 carbon atoms and optionally containing one or more heteroatoms, phenyl, benzyl, or pyridinyl; or $R_2$ and $R_3$ (in case $R_2$ is different than H) may be part of the same cyclic group containing from 3 to 8 carbon atoms; R' and R" are independently H or an aliphatic hydrocarbon group containing from 1 to 12 carbon atoms; and b) a molecular weight from 600 to 20000 Daltons, wherein the molecular weight is determined using MALDI-TOF mass spectrometry according to the description.

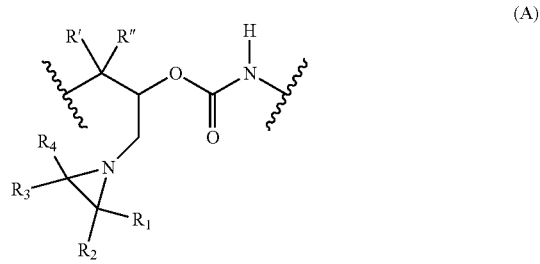

(A)

22 Claims, No Drawings

(51) Int. Cl.

| | | |
|---|---|---|
| C07D 403/12 | (2006.01) | |
| C07D 403/14 | (2006.01) | |
| C07D 413/14 | (2006.01) | |
| C07D 487/14 | (2006.01) | |
| C08F 220/18 | (2006.01) | |
| C08G 18/02 | (2006.01) | |
| C08G 18/08 | (2006.01) | |
| C08G 18/12 | (2006.01) | |
| C08G 18/22 | (2006.01) | |
| C08G 18/24 | (2006.01) | |
| C08G 18/28 | (2006.01) | |
| C08G 18/30 | (2006.01) | |
| C08G 18/32 | (2006.01) | |
| C08G 18/34 | (2006.01) | |
| C08G 18/38 | (2006.01) | |
| C08G 18/42 | (2006.01) | |
| C08G 18/44 | (2006.01) | |
| C08G 18/48 | (2006.01) | |
| C08G 18/66 | (2006.01) | |
| C08G 18/67 | (2006.01) | |
| C08G 18/73 | (2006.01) | |
| C08G 18/75 | (2006.01) | |
| C08G 18/76 | (2006.01) | |
| C08G 18/79 | (2006.01) | |
| C08G 18/83 | (2006.01) | |
| C08K 5/3412 | (2006.01) | |
| C08K 5/3492 | (2006.01) | |
| C08L 63/00 | (2006.01) | |
| C09D 7/20 | (2018.01) | |
| C09D 7/45 | (2018.01) | |
| C09D 7/63 | (2018.01) | |
| C09D 7/65 | (2018.01) | |
| C09D 11/101 | (2014.01) | |
| C09D 133/02 | (2006.01) | |
| C09D 133/04 | (2006.01) | |
| C09D 175/04 | (2006.01) | |
| C09D 175/08 | (2006.01) | |
| C09D 175/12 | (2006.01) | |

(52) U.S. Cl.
CPC ......... *C07D 403/14* (2013.01); *C07D 413/14* (2013.01); *C07D 487/14* (2013.01); *C08F 220/1804* (2020.02); *C08G 18/027* (2013.01); *C08G 18/0823* (2013.01); *C08G 18/0866* (2013.01); *C08G 18/12* (2013.01); *C08G 18/227* (2013.01); *C08G 18/246* (2013.01); *C08G 18/282* (2013.01); *C08G 18/2825* (2013.01); *C08G 18/283* (2013.01); *C08G 18/2865* (2013.01); *C08G 18/2875* (2013.01); *C08G 18/302* (2013.01); *C08G 18/3228* (2013.01); *C08G 18/3231* (2013.01); *C08G 18/3275* (2013.01); *C08G 18/348* (2013.01); *C08G 18/3842* (2013.01); *C08G 18/4291* (2013.01); *C08G 18/44* (2013.01); *C08G 18/4808* (2013.01); *C08G 18/4825* (2013.01); *C08G 18/4854* (2013.01); *C08G 18/4862* (2013.01); *C08G 18/4879* (2013.01); *C08G 18/6692* (2013.01); *C08G 18/6715* (2013.01); *C08G 18/73* (2013.01); *C08G 18/755* (2013.01); *C08G 18/758* (2013.01); *C08G 18/765* (2013.01); *C08G 18/792* (2013.01); *C08G 18/798* (2013.01); *C08G 18/833* (2013.01); *C08K 5/3412* (2013.01); *C08K 5/34924* (2013.01); *C08K 5/34926* (2013.01); *C08L 63/00* (2013.01); *C09D 7/20* (2018.01); *C09D 7/45* (2018.01); *C09D 7/63* (2018.01); *C09D 7/65* (2018.01); *C09D 11/101* (2013.01); *C09D 133/02* (2013.01); *C09D 133/04* (2013.01); *C09D 175/04* (2013.01); *C09D 175/08* (2013.01); *C09D 175/12* (2013.01); *C08G 2150/00* (2013.01)

(58) Field of Classification Search
CPC .............. C08G 18/2825; C08G 18/283; C08G 18/2865; C08G 18/348; C08G 18/3842
See application file for complete search history.

(56) References Cited

U.S. PATENT DOCUMENTS

| | | | |
|---|---|---|---|
| 3,523,750 A | 8/1970 | Tesoro | |
| 3,560,415 A | 2/1971 | Grögler et al. | |
| 3,583,977 A | 6/1971 | Uelzmann | |
| 3,763,132 A | 10/1973 | Meiser | |
| 3,933,936 A | 1/1976 | Smith et al. | |
| 4,605,698 A | 8/1986 | Briden | |
| 5,106,993 A | 4/1992 | Kania | |
| 5,133,997 A | 7/1992 | Maier et al. | |
| 5,164,467 A | 11/1992 | Kania | |
| 5,241,001 A | 8/1993 | Kania et al. | |
| 5,258,481 A | 11/1993 | Hesselmans et al. | |
| 5,359,005 A | 10/1994 | Kania et al. | |
| 5,712,331 A | 1/1998 | Ryang | |
| 7,294,449 B1 | 11/2007 | Guideman et al. | |
| 7,396,891 B2 | 7/2008 | Gray et al. | |
| 8,318,855 B2 | 11/2012 | Schafheutle et al. | |
| 9,695,481 B2 | 7/2017 | Van de Water et al. | |
| 2003/0229176 A1 | 12/2003 | Trombetta et al. | |
| 2006/0117991 A1 | 6/2006 | Mayo et al. | |
| 2006/0148980 A1 | 7/2006 | Tielemans et al. | |
| 2007/0298006 A1 | 12/2007 | Tomalia et al. | |
| 2008/0114096 A1 | 5/2008 | Qu et al. | |
| 2009/0318615 A1* | 12/2009 | Schafheutle | C08G 18/0823 524/839 |
| 2010/0227945 A1 | 9/2010 | Bissinger et al. | |
| 2011/0086180 A1 | 4/2011 | Tielemans | |
| 2012/0059076 A1* | 3/2012 | Olang | B29C 44/3442 521/76 |
| 2015/0118501 A1 | 4/2015 | Lu et al. | |
| 2017/0218110 A1 | 8/2017 | Arzt et al. | |

FOREIGN PATENT DOCUMENTS

| | | |
|---|---|---|
| CN | 1720223 A | 1/2006 |
| CN | 1823110 A | 8/2006 |
| CN | 101365688 A | 2/2009 |
| CN | 101437863 A | 5/2009 |
| CN | 101619164 A | 1/2010 |
| CN | 102046688 A | 5/2011 |
| CN | 104080861 A | 10/2014 |
| CN | 104379618 A | 2/2015 |
| CN | 105143297 A | 12/2015 |
| CN | 105377918 A | 3/2016 |
| CN | 105705598 A | 6/2016 |
| CN | 107922762 A | 4/2018 |
| CN | 108084870 | 5/2018 |
| CN | 110023354 A | 7/2019 |
| CN | 110248977 A | 9/2019 |
| CN | 110607120 A | 12/2019 |
| CN | 112469755 A | 3/2021 |
| CN | 117015566 A | 11/2023 |
| CN | 117836343 A | 4/2024 |
| EP | 0 227 461 | 7/1987 |
| EP | 0 507 407 | 10/1992 |
| EP | 0 758 662 | 2/1997 |
| EP | 1 865 014 | 12/2007 |
| EP | 2 616 484 | 7/2013 |
| GB | 1 344 725 | 1/1974 |
| JP | 47-027971 | 8/1972 |
| JP | 51-141860 | 5/1976 |
| JP | 59-128291 | 7/1984 |

(56) References Cited

FOREIGN PATENT DOCUMENTS

| | | |
|---|---|---|
| JP | S59 128291 | 7/1984 |
| JP | 11-500152 | 1/1999 |
| JP | 2012-529473 | 11/2012 |
| JP | 2015-505889 | 2/2015 |
| KR | 1020060066442 A | 6/2006 |
| NL | 9100578 | 4/1992 |
| WO | 2006/115547 | 11/2006 |
| WO | 2008069298 A1 | 6/2008 |
| WO | 2013/089927 | 6/2013 |
| WO | 2015/066868 | 5/2015 |
| WO | 2017216767 A1 | 12/2017 |
| WO | 2020/020714 | 1/2020 |

OTHER PUBLICATIONS

Written Opinion of the ISA for PCT/EP2021/051392 dated Apr. 14, 2021 (7 pages).
Dahlquist et al., "Contact allergy to trimethylolpropane triacrylate (TMPTA) in an aziridine plastic hardener", Contact Dermatitis, 1983, pp. 122-124, vol. 9.
Fei et al., "Properties and Curing Kinetic of Acrylic Resin Cured with Aziridine Crosslinker", Chinese Journal of Synthetic Chemistry, 2002, pp. 120-125, vol. 10, Issue 2.
Haitao et al., "Synthesis and Application of Aziridine Crosslinking Agent in Waterborne Coatings", Shanghai Coatings, 2013, 7 pages, vol. 51, No. 10.
Jiao, "Preparation of Waterborne Polyurethane Based on Renewable Resources and Its Film Properties", Masteral Dissertation, Dalian University of Technology, 2010, 79 pages.
Lee et al., "Preparation and characterization of acrylic pressure-sensitive adhesives based on UV and heat curing systems", International Journal of Adhesion and Adhesives, 2017, 21 pages.
Qingfang et al., "Study on heat resistance of polyurethane-imide/organosilicon modified epoxy coatings", Synthetic Materials and Applications, 2018, 5 pages, vol. 47, No. 3.
Walsh et al., "Polyamine-Functional Sterically Stabilized Latexes for Covalently Cross-Linkable Colloidosomes", Langmuir, 2010, pp. 18039-18048, vol. 26(23).
Wang et al., "Pervaporation Properties to Aromatic/Non-Aromatic Hydrocarbon Mixtures of Cross-Linked Membranes of Copoly(methacrylates) with Pendant Phosphate and Carbamoylphosphonate Groups", Journal of Membrane Science, 2002, pp. 13-27, vol. 199.
Yoo et al., "Preparation of Acrylic Copolymers and Crosslinking Agents and Properties as a Film", Journal of Applied Polymer Science, 2009, pp. 1587-1594, vol. 112.
Zilin et al., "Effect of Crosslinking Agent on Waterborne Polyurethane Wet Friction Fixing Agent", Shandon Chemical Industry, 2019, pp. 1-4, vol. 8, Issue 14.

* cited by examiner

MULTI-AZIRIDINE COMPOUND

This application is the U.S. national phase of International Application No. PCT/EP2021/051392 filed Jan. 21, 2021 which designated the U.S. and claims priority to EP 20153240.5 filed Jan. 22, 2022, EP 20187717.2 filed Jul. 24, 2020, EP 20153628.1 filed Jan. 24, 2020, EP 20153630.7 filed Jan. 24, 2020, EP 20153154.8 filed Jan. 22, 2020, EP 20153159.7 filed Jan. 22, 2020, EP 20153239.7 filed Jan. 22, 2020, EP 20153242.1 filed Jan. 22, 2020, EP 20153245.4 filed Jan. 22, 2020, EP 20153246.2 filed Jan. 22, 2020, EP 20153249.6 filed Jan. 22, 2020, EP 20153250.4 filed Jan. 22, 2020, EP 20153251.2 filed Jan. 22, 2020, EP 20153253.8 filed Jan. 22, 2020, the entire contents of each of which are hereby incorporated by reference.

The present invention relates to multi-aziridine compounds which can be used for crosslinking of carboxylic acid functional polymers dissolved and/or dispersed in an aqueous medium.

Coatings provide protection, aesthetic quality and new functionality to a wide range of substrates with tremendous industrial and household relevance. In this context, the need for coatings with improved resistances, like stain and solvent resistance, improved mechanical properties and improved adhesive strength is growing continuously. One or more of those properties can be enhanced by means of crosslinking. Many crosslinking mechanisms for polymeric binders have been studied over the years and for waterborne latex polymer dispersions, the most useful ones include isocyanate crosslinking of hydroxyl functional polymers, carbodiimide crosslinking of carboxylic acid functional polymers, melamine crosslinking, epoxy crosslinking and aziridine crosslinking of carboxylic acid functional polymers.

Waterborne binders are generally colloidal stabilized by carboxylic acid groups, and the coating properties can be improved by the use of carbodiimide or aziridine crosslinkers since they react with the carboxylic acid moieties of the polymer resulting in a crosslinked network. Of the state-of-the-art crosslinkers as mentioned above, aziridine crosslinkers are most versatile for room temperature curing of carboxylic acid functional polymers.

U.S. Pat. No. 5,133,997 describes coating compositions comprising an aqueous dispersion of linear aliphatic urethane resins, an anionic surfactant and a crosslinking agent capable of facilitating the cure of said resin. Trimethylolpropane tris(2-methyl-1-aziridinepropionate), CAS number 64265-57-2, a polyfunctional aziridine crosslinker, is used as crosslinking agent, which is a well-known and very active crosslinker for crosslinking carboxylic acid functional polymers. This crosslinker, like other state-of-the-art aziridines such as XAMA-7 (pentaerythritol tris[3-(1-aziridinyl)propionate; CAS No. 57116-45-7), has an unfavourable genotoxic profile. There is a need in the industry to improve the safety, health and environmental profile of adhesives, inks and coatings and also of the substances used for preparing adhesives, inks and coatings. Genotoxicity describes the property of chemical or physical agents that cause any type of DNA damage, which may not always lead to a transmittable mutation. Mutagenicity refers to the induction of permanent transmissible DNA changes (as DNA composition or chromosome structure), which are retained in somatic cell division and passed onto progeny in germ cells. Genotoxicity must not be confused with mutagenicity. All mutagens are genotoxic whereas not all genotoxic substances are mutagenic.

Additionally, traditional crosslinking approaches generally involve the use of reactive organic molecules of low molecular weight, occasionally dissolved in volatile organic solvents for reducing viscosity to facilitate accurate dosing and mixing of the crosslinker to/in the polymer composition to be crosslinked. Good miscibility of the crosslinker with the polymer composition is important for both the final properties (poor miscibility tends to give inefficient crosslinking) and for efficiency and convenience of the user of the material. However, the use of volatile organic solvents to reduce viscosity is undesirable since this will increase the VOC (Volatile Organic Compounds) levels. Further, the presence of solvents in the crosslinker composition will reduce the formulation latitude of the formulator of the coating composition and is therefore undesirable. It would therefore be beneficial to deliver multi-aziridine crosslinkers in water. At the same time, crosslinker performance needs to be preserved, in terms of crosslinking efficiency and storage stability, to remain commercially feasible in a variety of polymeric resins.

The object of the present invention is to provide a compound with at least two aziridinyl groups which has reduced genotoxicity compared to trimethylolpropane tris (2-methyl-1-aziridinepropionate) and with good crosslinking efficiency. Compounds with at least two aziridinyl groups are further referred herein as multi-aziridine compounds.

It has surprisingly been found that this object can be achieved by providing a multi-aziridine compound having:
a) at least 2 of the following structural units (A):

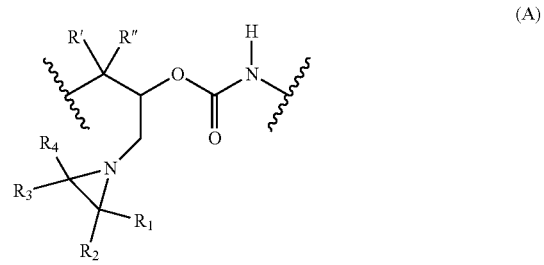

whereby
$R_1$ is H;
$R_2$ and $R_4$ are independently chosen from H, a linear group containing from 1 to 8 carbon atoms and optionally containing one or more heteroatoms, a branched or cyclic group containing from 3 to 8 carbon atoms and optionally containing one or more heteroatoms, phenyl, benzyl, or pyridinyl;
$R_3$ is chosen from a linear group containing from 1 to 8 carbon atoms and optionally containing one or more heteroatoms, a branched or cyclic group containing from 3 to 8 carbon atoms and optionally containing one or more heteroatoms, phenyl, benzyl, or pyridinyl;
or $R_2$ and $R_3$ (in case $R_2$ is different than H) may be part of the same cyclic group containing from 3 to 8 carbon atoms;
R' and R" are independently H or an aliphatic hydrocarbon group containing from 1 to 12 carbon atoms; and
b) a molecular weight from 600 to 20000 Daltons, wherein the molecular weight is determined using MALDI-TOF mass spectrometry according to the description; and the multi-aziridine compound is obtained by reacting at least a polyisocyanate and a compound (B) with the following structural formula:

whereby n is an integer equal to or larger than 2, Z is an n-valent radical or a mixture of n-valent radicals and D has the following structural formula:

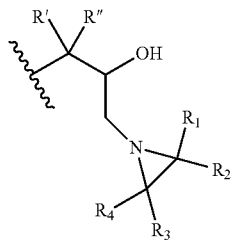

whereby the molar ratio of moiety D to isocyanate moieties on polyisocyanates is from 0.5 to 2.

It has surprisingly been found that the multi-aziridine compounds according to the invention have reduced genotoxicity compared to trimethylolpropane tris(2-methyl-1-aziridinepropionate) while also having good crosslinking efficiency. The multi-aziridine compounds according to the invention show either only weakly positive induced genotoxicity or even they do not show genotoxicity, i.e. they show a genotoxicity level comparable with the naturally occurring background. Preferably, these compounds can also be delivered and stored in water with a longer shelf life while maintaining sufficient reactivity towards carboxylic acid functional polymers.

The genotoxicity can be measured by the ToxTracker® assay (Toxys, Leiden, the Netherlands) as further described herein. The ToxTracker® assay can be applied for pure substances or for compositions which are the direct products obtained in the preparation of the multi-aziridine compounds of the invention. With positive induced genotoxicity is meant that the induction level of the biomarkers Bscl2-GFP and Rtkn-GFP is equal to or higher than 2-fold at at least one of 10, 25 and 50% cytotoxicity in the absence or presence of the metabolizing system rat S9 liver extract. With weakly positive induced genotoxicity is meant that the induction level of the biomarkers Bscl2-GFP and Rtkn-GFP is higher than 1.5-fold and lower than 2-fold at at least one of 10, 25 and 50% cytotoxicity (but lower than 2-fold at 10, 25 and 50% cytotoxicity) in the absence or presence of rat S9 liver extract-based metabolizing systems (aroclor1254-induced rats, Moltox, Boone, NC, USA). With genotoxicity comparable with the naturally occurring background is meant that the induction level of the biomarkers Bscl2-GFP and Rtkn-GFP is less than or equal to 1.5-fold at 10, 25 and 50% cytotoxicity in the absence and presence of rat S9 liver extract-based metabolizing systems (aroclor1254-induced rats, Moltox, Boone, NC, USA). The induction level of the genotoxicity reporters Bscl2-GFP and Rtkn-GFP is preferably less than or equal to 1.5-fold at 10, 25 and 50% cytotoxicity in the absence and presence of rat S9 liver extract-based metabolizing systems (aroclor1254-induced rats, Moltox, Boone, NC, USA). A substance showing an induction level less than or equal to 1.5-fold at 10, 25 and 50% cytotoxicity in the absence and presence of rat S9 liver extract-based metabolizing systems (aroclor1254-induced rats, Moltox, Boone, NC, USA) is not genotoxic.

Crosslinking efficiency of a crosslinker can be assessed by assessing the chemical resistance defined and determined as described below.

For all upper and/or lower boundaries of any range given herein, the boundary value is included in the range given, unless specifically indicated otherwise. Thus, when saying from x to y, means including x and y and also all intermediate values.

The term "coating composition" encompasses, in the present description, paint, coating, varnish, adhesive and ink compositions, without this list being limiting. Self-crosslinkable coating compositions are crosslinkable without the requirement for mixing reactive materials just prior to application which react with groups on the crosslinkable polymer, although such external triggers can still be employed if desired. The term "aliphatic hydrocarbon group" refers to optionally branched alkyl, alkenyl and alkynyl group. The term "cycloaliphatic hydrocarbon group" refers to cycloalkyl and cycloalkenyl group optionally substituted with at least one aliphatic hydrocarbon group. The term "aromatic hydrocarbon group" refers to a benzene ring optionally substituted with at least one aliphatic hydrocarbon group. These optional aliphatic hydrocarbon group substituents are preferably alkyl groups. Examples of cycloaliphatic hydrocarbon groups with 7 carbon atoms are cycloheptyl and methyl substituted cyclohexyl. An example of an aromatic hydrocarbon group with 7 carbon atoms is methyl substituted phenyl. Examples of aromatic hydrocarbon groups with 8 carbon atoms are xylyl and ethyl substituted phenyl.

Whilst the structural units (A) present in the multi-aziridine compound according to the invention may independently have different $R_2$, $R_3$, $R_4$, R' and/or R", the structural units (A) present in the multi-aziridine compound are preferably identical to each other.

The multi-aziridine compound according to the invention is usually obtained in a composition in which, next to the multi-aziridine compound, remaining starting materials, side-products and/or solvent used for preparing the multi-aziridine compounds may be present. The composition may contain only one multi-aziridine compound according to the invention but may also contain more than one multi-aziridine compound according to the invention. Mixtures of multi-aziridine compounds are for example obtained when a mixture of polyisocyanates as starting material are used.

The multi-aziridine compound according to the invention preferably contains from 2 to 50 of the structural units (A), more preferably from 2 to 10 of the structural units (A) and even more preferably from 2 to 4 of the structural units (A).

$R_1$ is H. Preferably, $R_2$ and $R_4$ are independently chosen from H or an aliphatic hydrocarbon group containing from 1 to 4 carbon atoms. More preferably, $R_2$ and $R_4$ are independently chosen from H or an aliphatic hydrocarbon group containing from 1 to 2 carbon atoms. Preferably, $R_3$ is an aliphatic hydrocarbon group containing from 1 to 4 carbon atoms, more preferably an aliphatic hydrocarbon group containing from 1 to 2 carbon atoms.

In a preferred embodiment of the invention, $R_2$ is H, $R_3$ is $C_2H_5$ and $R_4$ is H. In another and more preferred embodiment of the invention, $R_2$ is H, $R_3$ is $CH_3$ and $R_4$ is H or $CH_3$. In another and even more preferred embodiment of the invention, $R_2$ is H, $R_3$ is $CH_3$ and $R_4$ is H.

Preferably, R' and R" are H.

The multi-aziridine compound has a molecular weight from 600 to 200000 Daltons.

Preferably the multi-aziridine compound has a molecular weight of at least 800 Daltons, more preferably at least 840

Daltons, even more preferably at least 1000 Daltons and preferably at most 10000 Daltons, more preferably at most 5000 Daltons.

The multi-aziridine compound of the present invention is obtained by reacting at least a polyisocyanate and a compound (B) with the following structural formula:

$$Z\text{-}[D]_n$$

whereby n is an integer equal to or larger than 2, Z is an n-valent radical or a mixture of n-valent radicals and D has the following structural formula:

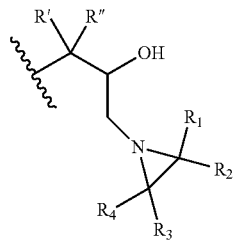

whereby the molar ratio of moiety D to isocyanate moieties on polyisocyanates is from 0.5 to 2, and whereby R', R", $R_1$, $R_2$, $R_3$ and $R_4$ are defined above.

Preferably, Z is an n-valent radical consisting of a collection of atoms covalently connected in linear or branched configuration, which collection of atoms consists of i) carbon and hydrogen atoms, ii) carbon, hydrogen and oxygen atoms, iii) carbon, hydrogen and nitrogen atoms, or iv) carbon, hydrogen, oxygen and nitrogen atoms, or wherein Z is a mixture of such n-valent radicals.

Preferably n in $Z\text{-}[D]_n$ is 2 and $Z\text{-}[D]_n$ is:

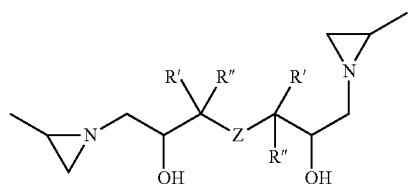

Reacting the polyisocyanate with compound B may be carried out by bringing appropriate amounts of the polyisocyanate into contact with the compound B at a temperature in the range of from 0 to 110° C., more suitable from 20° C. to 110° C., more suitable from 40° C. to 95° C., even more suitable from 60 to 85° C. in the presence of for example a tin catalyst such as for example dibutyltin dilaurate or a bismuth catalyst such as for example bismuth neodecanoate. A solvent may be used, such as for example dimethylformamide DMF, acetone and/or methyl ethyl ketone. The polyisocyanate preferably contains 2 isocyanate groups on average. Mixtures of polyisocyanates may also be used as starting materials. Polyisocyanates with aromatic reactivity can be used such as for example 4,4'diphenylmethane-diisocyanate, 2,4-toluene-diisocyanate and 2,6-toluene-diisocyanate and mixtures thereof. Preferred polyisocyanates are polyisocyanates with aliphatic reactivity. The term "a polyisocyanate with aliphatic reactivity" being intended to mean compounds in which all of the isocyanate groups are directly bonded to aliphatic or cycloaliphatic hydrocarbon groups, irrespective of whether aromatic hydrocarbon groups are also present. The polyisocyanate with aliphatic reactivity can be a mixture of polyisocyanates with aliphatic reactivity. Preferred polyisocyanates with aliphatic reactivity are 1,5-pentamethylene diisocyanate, 1,6-hexamethylene diisocyanate, isophorone diisocyanate, 4,4'-dicyclohexyl methane diisocyanate, 2,2,4-trimethyl hexamethylene diisocyanate, 2,4,4-trimethyl hexamethylene diisocyanate, p-tetra-methylxylene diisocyanate (p-TMXDI) and its meta isomer.

Compound B can be prepared by the reaction of a polyepoxide with an aziridine. The reaction takes places at any temperature from 20 to 110° C., more preferably from 50 to 95° C., and most preferably from 70 to 90° C. and its progress can be monitored via $^1$H-NMR spectroscopy. The reaction is carried out for as long as the epoxy groups are reacted; this is monitored and verified by $^1$H-NMR spectroscopy where the characteristic $^1$H-NMR chemical shift of the epoxy protons (2.5-3 ppm) is disappeared. Preferably the reaction is carried out without solvent. However, if desired (for instance to reduce the viscosity), one or more solvents e.g. methanol, ethanol, toluene, can be used during or after the reaction. If solvent is used, it is often convenient to first dissolve the polyepoxide in the solvent (or mixture of solvents) before adding the aziridine to the reaction mixture. The molar ratio of the aziridine groups to the epoxy groups of the polyepoxide is at least 1 and at most 8, more preferably at least 1 and at most 4, even more preferably at least 1.1 and at most 3 and most preferably at least 1.2 and at most 2.2. Once the reaction is completed, the residual aziridine is distilled off, preferably at a temperature from 60 to 90° C., more preferably from 65 to 80° C., and at a reduced pressure, for example from 20 to 50 mbar, preferably from 30 to 45 mbar. Preferably once the reaction is completed, the residual aziridine is distilled off at a reduced pressure from 20 to 50 mbar at 70° C., more preferably from 30 to 45 mbar at 70° C. Subsequently, a further distillation step for the removal of any unreacted aziridine and any other volatiles is carried out at 25 to 40° C. at 2 to 4 mbar, until no aziridine could be detected by $^1$H-NMR spectroscopy. It is often useful to add an additional solvent to the reaction mixture prior or during distillation, to facilitate the removal of the excess of the aziridine. If desired, a base can be used during the reaction, to reduce possible sources of acid. Bases include both organic bases, like tertiary amines or inorganic bases like sodium or potassium carbonate or for instance calcium hydroxide. The inorganic bases can be filtered off after the reaction is completed.

Non-limiting examples of polyepoxide compounds used for preparing compound B are bisphenol AP diglycidyl ether, bisphenol AF diglycidyl ether, bisphenol B diglycidyl ether, bisphenol BP diglycidyl ether, bisphenol C diglycidyl ether, bisphenol C2 diglycidyl ether, bisphenol E diglycidyl ether, bisphenol F diglycidyl ether, bisphenol G diglycidyl ether, bisphenol M diglycidyl ether, bisphenol S diglycidyl ether, bisphenol P diglycidyl ether, bisphenol PH diglycidyl ether, bisphenol TMC diglycidyl ether, bisphenol Z diglycidyl ether, dinitrobisphenol A diglycidyl ether, tetrabromobisphenol A diglycidyl ether, Bisphenol A diglycidyl ether, Hydrogenated Bisphenol A diglycidyl ether, Neopentyl glycol diglycidyl ether, butanediol diglycidyl ether, ethylene glycol diglycidyl ether, 1,6-Hexanediol diglycidyl ether, polypropyleneglycol diglycidyl ether, Poly(ethylene glycol) diglycidyl ether and any mixture thereof.

Preferred polyepoxide compounds used for preparing compound B are Bisphenol A diglycidyl ether (CAS 1675-54-3), Hydrogenated Bisphenol A diglycidyl ether (CAS 30583-72-3), Neopentyl glycol diglycidyl ether (CAS 17557-23-2), butanediol diglycidyl ether (CAS 2425-79-8), ethylene glycol diglycidyl ether (CAS 2224-15-9), 1,6-

Hexanediol diglycidyl ether (CAS 16096-31-4), polypropyleneglycol diglycidyl ether (CAS 26142-30-3), Poly(ethylene glycol) diglycidyl ether (CAS 72207-80-8) and any mixture thereof.

Preferred aziridine compounds used for preparing compound B are propylene imine and ethylaziridine. Synthesis of ethylaziridine is for example described in EP0227461 B1. Most preferred aziridine compounds used for preparing compound B is propylene imine.

The multi-aziridine compound can also be obtained by reacting at least a compound B with a polyisocyanate as defined above and a polyol and/or a polyamine. The multi-aziridine compound can also be obtained by reacting the polyisocyanate as defined above with a polyol and/or a polyamine and reacting the so-obtained compound with compound B. The multi-aziridine compound can also be obtained by reacting compound B with the polyisocyanate and reacting the so obtained compound with a polyol and/or a polyamine. The multi-aziridine compound can also be obtained by reacting at least a compound B with an isocyanate terminated polyurethane and/or a polyurethane urea. The (isocyanate terminated) polyurethane (urea) is obtained by reacting at least one polyol and/or polyamine with at least one polyisocyanate. Preferred polyisocyanates are as described above. Preferably the multi-aziridine compound is end capped with any of the following, a monofunctional alcohol or amine. Non limiting examples can be ethanol, butanol, isopropanol, propanol, cyclohexanol, n-methylbutylamine, or more preferably the adduct of a non-OH functional mono-epoxide and an aziridine according to structure E:

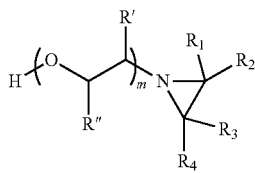

Compound E whereby $R_1$ is H,
$R_2$ and $R_4$ are independently chosen from H or an aliphatic hydrocarbon group containing from 1 to 4 carbon atoms,
$R_3$ is an aliphatic hydrocarbon group containing from 1 to 4 carbon atoms,
m is an integer from 1 to 6,
R' and R'' are according to (1) or (2):
(1) R'=H or an aliphatic hydrocarbon group containing from 1 to 14 carbon atoms, and
R''=H, an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, $CH_2$—O—(C=O)—R''', $CH_2$—O—R'''', or $CH_2$—(OCR''''HCR''''H)$_n$—OR''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R'''' independently being H or an aliphatic hydrocarbon group containing from 1 to 14 carbon atoms and R''''' being an aliphatic hydrocarbon group containing from 1 to 4 carbon atoms, (2) R' and R'' form together a saturated cycloaliphatic hydrocarbon group containing from 5 to 8 carbon atoms.

Non-limited examples of non-OH functional mono-epoxides are ethylene oxide, propylene oxide, 2-ethyl oxirane, n-butylglycidylether, 2-ethylhexylglycidylether, phenyl glycidyl ether, 4-tert-butylphenyl 2,3-epoxypropyl ether (=t-butyl phenyl glycidyl ether), cresol glycidyl ether (ortho or para) and glycidyl neodecanoate. The non-OH functional monoepoxide is preferably selected from the group consisting of ethylene oxide (CAS number 75-21-8), propylene oxide (CAS number 75-56-9), 2-ethyl oxirane (CAS number 106-88-7), n-butylglycidylether (CAS number 2426-08-6), 2-ethylhexylglycidylether (CAS number 2461-15-6), glycidyl neodecanoate (CAS number 26761-45-5) and any mixture thereof. More preferably, the non-OH functional monoepoxide is selected from the group consisting of propylene oxide (CAS number 75-56-9), 2-ethyl oxirane (CAS number 106-88-7), n-butylglycidylether (CAS number 2426-08-6), 2-ethylhexylglycidylether (CAS number 2461-15-6), glycidyl neodecanoate (CAS number 26761-45-5) and any mixture thereof.

Alternatively, the multi-aziridine compound is end-capped with a monofunctional isocyanate.

The polyol is preferably selected from the group consisting of polyether polyols, polyester polyols, polythioether polyols, polycarbonate polyols, polyacetal polyols, polyvinyl polyols, polysiloxane polyols and any mixture thereof. More preferably the polyol is selected from the group consisting of polyether polyols and any mixture thereof. Preferred polyether polyols are polytetrahydrofuran, polyethylene oxide, polypropylene oxide or any mixture thereof. More preferred polyether polyols is poly(propyleneglycol). The amount of polyoxyethylene (—O—CH2-CH2-)$_x$, polyoxypropylene (—O—CHCH3-CH2-)$_x$ or (—O—CH2-CH2-CH2-)$_x$ group(s) and/or polytetrahydrofurane (—O—CH2-CH2-CH2-CH2)$_x$ groups in the multi-aziridine compound is preferably at least 6 wt. %, more preferably at least 10 wt. % and preferably less than 45 wt. %, more preferably less than 40 wt. % and most preferably less than 35 wt. %, relative to the total weight of the multi-aziridine compound. x represents an average addition mole number of oxyethylene, oxypropylene resp. tetrahydrofurane and x is preferably an integer from 5 to 20. The polyamine is preferably selected from the group consisting of polyether polyamines, polyester polyamines, polythioether polyamines, polycarbonate polyamines, polyacetal polyamines, polyvinyl polyamines, polysiloxane polyamines and any mixture thereof. More preferably the polyamine is selected from the group consisting of polyether polyamines and any mixture thereof. Preferred polyether polyamines are Jeffamine® D-230, Jeffamine® D-400 and Jeffamine® D-2000. The use of a polyol is preferred over the use of a polyamine.

Optionally, the multi-aziridine compound contains ionic groups. These can for example be incorporated using the following, non-limiting examples of building blocks: 3-(Cyclohexylamino)-1-propanesulfonic acid (CAPS, CAS No 1135-40-6), 2-(Cyclohexylamino)ethanesulfonic acid (CHES, CAS No 103-47-9), and taurine (CAS No 107-35-7).

Examples of preferred multi-aziridine compounds according to the invention are shown below:

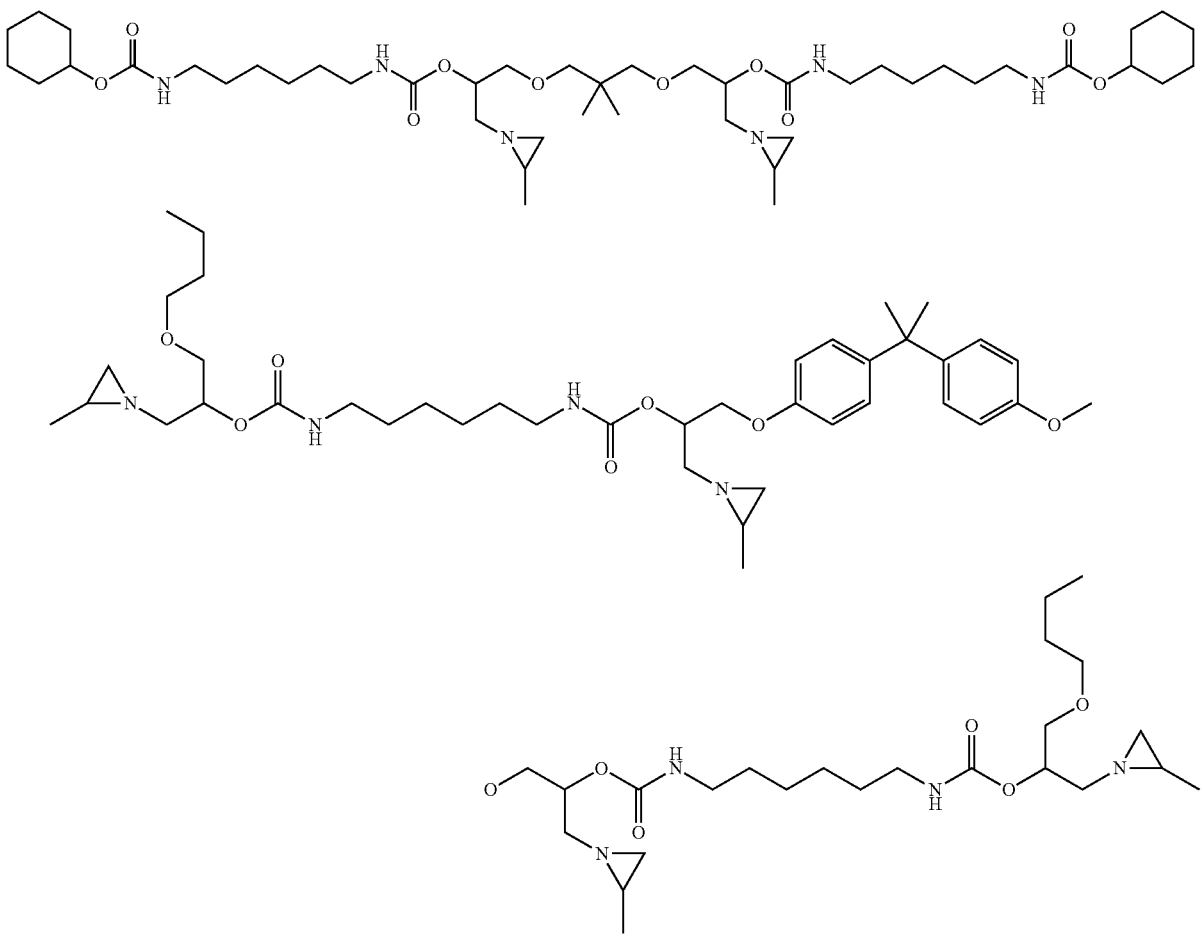

An aziridinyl group has the following structural formula:

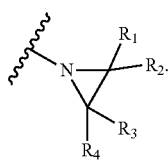

A further aspect of the current invention is a crosslinker composition comprising at least one multi-aziridine compound as defined above and further comprising at least one additional component, such as for example remaining starting materials, side-products and/or solvent used for preparing the multi-aziridine compound according to the invention. The crosslinker composition may contain only one multi-aziridine compound according to the invention but may also contain more than one multi-aziridine compound according to the invention. After having obtained the multi-aziridine compound(s) according to the invention, the multi-aziridine compound(s) according to the invention may be separated, the reaction product may be used without further purification or solvent used for preparing the multi-aziridine compound(s) may be removed from the composition obtained in the preparation of the multi-aziridine compound(s) of the invention. The amount of multi-aziridine compounds according to the invention in the crosslinker composition is usually at least 10 wt. %, usually often at least 15 wt. % and most often at least 25 wt. % relative to total amount of the composition. The amount of multi-aziridine compounds according to the invention in the crosslinker composition is preferably at least 60 wt. %, more preferably at least 80 wt. % and most preferably at least 99 wt. %, relative to total amount of the crosslinker composition. The amount of aziridinyl group functional molecules, present in the crosslinker composition according to the invention, having a molecular weight lower than 580 Daltons is lower than 5 wt. %, preferably lower than 2 wt %, more preferably lower than 1 wt %, more preferably lower than 0.5 wt %, more preferably lower than 0.1 wt %, relative to the total weight of the crosslinker composition, whereby the molecular weight is determined using LC-MS as described in the experimental part below.

A further aspect of the present invention is a two-component coating system comprising a first component and a second component which is separate and distinct from each other, wherein the first component comprising a carboxylic acid functional polymer dissolved and/or dispersed, preferably dispersed, in an aqueous medium and wherein the second component comprising a multi-aziridine compound as defined above or wherein the second component is a crosslinker composition as defined above, whereby the first and second component are separately stored, since the crosslinking reaction between the crosslinking agent and the polymer to be crosslinked may start immediately after mixing the crosslinking agent with the aqueous composition of polymer to be crosslinked.

The carboxylic acid functional polymer contains carboxylic acid groups and/or carboxylate groups which are preferably free of a covalent bond that blocks these groups to chemically react with the aziridine moiety present in the multi-aziridine compound. As used herein, the amount of carboxylic acid groups present in the carboxylic acid functional polymer is the summed amount of deprotonated and protonated carboxylic acid groups present in the polymer to be crosslinked, i.e. in the carboxylic acid functional polymer. Thus, the amount of carboxylic acid groups present in the carboxylic acid functional polymer is the summed amount of carboxylate groups and carboxylic acid groups present in the carboxylic acid functional polymer. The polymer to be crosslinked preferably comprises carboxylate groups which are at least partially neutralized with base. Preferably at least part of the base is a volatile base. Preferably, at least a part of the carboxylic acid groups present in the carboxylic acid functional polymer to be crosslinked are subjected to deprotonation to obtain carboxylate groups. The deprotonation is effected by neutralizing the carboxylic acid functional polymer with a base. Examples of suitable bases are ammonia, secondary amines, tertiary amines, LiOH, NaOH and/or KOH. Examples of secondary amines and tertiary amines are described above. Preferred bases are tertiary amines. Preferred tertiary amines are as described above. Most preferred is triethylamine.

Non-limited examples of crosslinkable carboxylic acid functional polymers are vinyl polymers like styrene-acrylics, (meth)acrylic copolymers, vinyl acetate (co)polymers such as for example vinyl acetate vinyl chloride ethylene polymers, polyurethanes, polycondensates like polyesters, polyamides, polycarbonates and hybrids of any of these polymers where at least one of the two polymers have a carboxylic acid functionality. The carboxylic acid functional polymer is preferably selected from the group consisting of polyesters, polycarbonates, polyamides, vinyl polymers, polyacrylates, polymethacrylates, poly(acrylate-co-methacrylate)s, polyurethanes, poly(urethane-co-acrylate)s, poly(urethane-co-methacrylate)s, poly(urethane-co-acrylate-co-methacrylate), polyureas, and mixtures thereof. In an embodiment of the invention, preferred crosslinkable carboxylic acid functional polymers are selected from the group consisting of vinyl polymers, polyacrylates, polymethacrylates, poly(acrylate-co-methacrylate)s and mixtures thereof. Preferably by vinyl polymer is meant a polymer comprising reacted residues of styrene and acrylates and/or methacrylates. In another embodiment, the carboxylic acid functional polymer is selected from the group consisting of polyurethanes, poly(urethane-co-acrylate)s, poly(urethane-co-methacrylate)s, poly(urethane-co-acrylate-co-methacrylate), polyureas, and mixtures thereof. The present invention further also relates to a coating composition obtained by mixing the first and second component of the two-component coating system just prior to application of the coating composition, whereby the coating composition comprises aziridinyl groups Q and carboxylic acid groups in an amount such that the stoichiometric amount (SA) of aziridinyl groups Q on carboxylic acid groups is preferably from 0.1 to 2.0, more preferably from 0.2 to 1.5, even more preferably from 0.25 to 0.95, most preferably from 0.3 to 0.8. The pH of the coating composition is preferably at least 7.5, more preferably at least 8, more preferably at least 8.5 and even more preferably at least 9.

A further aspect of the present invention is an aqueous dispersion having a pH ranging from 8 to 14 and comprises particles X comprising multi-aziridine compound as defined herein above. It has surprisingly been found that the aqueous dispersion of the present invention has prolonged storage-stability, while at the same time still having good crosslinking efficiency in aqueous carboxylic acid functional polymer dispersions. The aqueous dispersions according to the invention shows efficient reaction with carboxylic acid groups at room temperature. The aqueous dispersions of the invention are also easy to use, its aqueous nature yielding good compatibility with waterborne binders and hence good mixing and low fouling during formulation. Further, these aqueous dispersions generally have low viscosities, resulting in facile handling and accurate dosing. The prolonged storage-stability in water, combined with a more favorable hazard profile, allows coatings manufacturers and applicators to easily and safely store and use the crosslinker composition in two-component 2K coating systems, where the binder and crosslinker diluted in aqueous medium are mixed shortly before application.

pH of the Aqueous Dispersion

The pH of the aqueous dispersion is at least 8. For further prolonging the shelf-life of the aqueous dispersion of the invention, it is beneficial that the pH is at least 8.5, preferably at least 9, more preferably at least 9.5. The pH of the aqueous dispersion is at most 14, preferably at most 13, more preferably at most 12 and even more preferably at most 11.5, since this allows to lower the amount of base present in the aqueous dispersion of the invention while the shelf-life of the aqueous dispersion remains sufficiently long. Most preferably, the pH of the aqueous dispersion is in the range from 9.5 to 11.5.

The aqueous dispersion preferably comprises ammonia, a secondary amine, a tertiary amine, LiOH, NaOH and/or KOH to adjust the pH to the desired value. Preferred amines are ammonia, secondary amines and/or tertiary amines. Examples of such secondary amines are, but not limited to, diisopropylamine, di-sec-butylamine and di-t-butylamine. More preferred amines are tertiary amines. Examples of such tertiary amines are, but not limited to, n-ethylmorpholine, n-methyl piperidine, n,n-dimethyl butyl amine, dimethyl isopropyl amine, dimethyl n-propyl amine, dimethyl ethylamine, triethylamine, dimethyl benzyl amine, n,n-dimethyl ethanolamine, 2-(diethylamino)ethanol, n,n-dimethyl isopropanol amine, 1-dimethylamino-2-propanol, 3-dimethylamino-1-propanol, 2-(dimethylamino)ethanol, 2-[2-(dimethylamino)ethoxy] ethanol. Preferred tertiary amines are n-ethylmorpholine, n-methyl piperidine, n,n-dimethyl butyl amine, dimethyl isopropyl amine, dimethyl n-propyl amine, dimethyl ethylamine, triethylamine and/or dimethyl benzyl amine. Most preferred is triethylamine.

The amount of water in the aqueous dispersion is preferably at least 15 wt. %, more preferably at least 20 wt. %, more preferably at least 30 wt. %, even more preferably at least 40 wt. %, on the total weight of the aqueous dispersion. The amount of water in the aqueous dispersion is preferably at most 95 wt. %, more preferably at most 90 wt. %, more preferably at most 85 wt. %, more preferably at most 80 wt. %, even more preferably at most 70 wt. %, even more preferably at most 60 wt. %, on the total weight of the aqueous dispersion.

The multi-aziridine compound as defined herein is present in the aqueous dispersion in an amount of preferably at least 5 wt. %, more preferably at least 10 wt. %, more preferably at least 15 wt. %, more preferably at least 20 wt. %, even more preferably at least 25 wt. %, even more preferably at least 30 wt. %, even more preferably at least 35 wt. %, on the total weight of the aqueous dispersion. The multi-aziridine compound as defined herein is present in the aqueous dispersion in an amount of preferably at most 70 wt. %, preferably at most 65 wt. %, more preferably at most 60 wt. %, even more preferably at most 55 wt. %, on the total weight of the aqueous dispersion.

Preferably at least 50 wt. %, more preferably at least 80 wt. %, even more preferably at least 95 wt. % and most preferably at least 99 wt. % of the multi-aziridine compound as defined herein is present in the aqueous dispersion in dispersed form. Accordingly, the aqueous dispersion of the invention comprises particles of the multi-aziridine compound as defined herein. Said particles preferably have a scatter intensity based average hydrodynamic diameter from 30 to 650 nanometer, more preferably from 50 to 500 nm, even more preferably from 70 to 350 nm, even more preferably from 120 to 275 nm. The scatter intensity based average hydrodynamic diameter of said particles may be controlled via a number of ways. For example, the scatter intensity based average hydrodynamic diameter of said particles may be controlled during the preparation of an aqueous dispersion of the invention by using different types of dispersants, and/or different amounts of dispersant(s), and/or by applying different shear stress, and/or by applying different temperature. For example, the scatter intensity based average hydrodynamic diameter of the particles is inversely dependent to the amount of the dispersant used in the preparation of an aqueous dispersion of the invention; for example, the scatter intensity based average hydrodynamic diameter of the particles decreases by increasing the amount of a dispersant. For example, the scatter intensity based average hydrodynamic diameter of the particles is inversely dependent to the shear stress applied during the preparation of an aqueous dispersion of the invention; for example, the scatter intensity based average hydrodynamic diameter of the particles decreases by increasing the shear stress. Exemplary dispersants include but are not limited to ATLAS™ G-5000, ATLAS™ G-5002L-LQ, Maxemul™ 7101 supplied by Croda.

The solids content of the aqueous dispersion is preferably at least 5, more preferably at least 10, even more preferably at least 20, even more preferably at least 30, even more preferably at least 35 wt. %. The solids content of the aqueous dispersion is preferably at most 70, preferably at most 65 and more preferably at most 55 wt. %. The solids content of the aqueous dispersion is most preferably in the range of from 35 to 55 wt. %.

The multi-aziridine compound as defined above is usually obtained in a composition in which, next to the multi-aziridine compound, remaining starting materials, side-products and/or solvent used in the preparation of the multi-aziridine compounds may be present. The composition may contain only one multi-aziridine compound as defined above but may also contain more than one multi-aziridine compound as defined above. Mixtures of multi-aziridine compounds are for example obtained when a mixture of polyisocyanates as starting material are used. The aqueous dispersion of the invention can be obtained by dispersing the multi-aziridine compound into water and adjusting the pH of the aqueous dispersion to the desired value or by dispersing the multi-aziridine compound into a mixture of water and at least one base which mixture has a pH such as to obtain an aqueous dispersion with the desired pH value or by adding a mixture of water and base to the multi-aziridine compound. Dispersing of the multi-aziridine in water or into a mixture of water and at least one base can be done using techniques well-known in the art. Solvents and/or high shear can be utilized in order to assist in the dispersion of the multi-aziridine compound.

The aqueous dispersion may further comprise organic solvent in an amount of at most 35 wt. %, preferably at most 30, for example at most 25, for example at most 20, for example at most 12, for example at most 10, for example at most 8, for example at most 5, for example at most 4, for example at most 3, for example at most 2, for example at most 1, for example at most 0.5, for example at most 0.2, for example at most 0.1 wt % on the total weight of the aqueous dispersion. Organic solvent may optionally be added before, during and/or after synthesis of the multi-aziridine(s). Organic solvent can be utilized in order to assist in dispersing the multi-aziridine compound in water. If desired, organic solvent can be removed afterwards from the cross-linker composition by reduced pressure and/or increased temperatures. Typical organic solvents are glycols, ethers, alcohols, cyclic carbonates, pyrrolidones, dimethylsulfoxide, n-formylmorpholine, dimethylacetamide, dimethylformamide and ketones. Preferred solvents are glycols, ethers, alcohols, cyclic carbonates and ketones.

Preferably the dispersing of the multi-aziridine compound is done in the presence of a dispersant. Accordingly, the aqueous dispersion of the invention preferably comprises a dispersant. In the context of the present invention, a dispersant is a substance that promotes the formation and colloidal stabilisation of a dispersion. In the present invention, said dispersant is preferably a species that is non-covalently attached to the multi-aziridine compound and/or said dispersant is a separate molecule component that is surface-active. Examples of species non-covalently attached to the multi-aziridine compound are urethane and/or urea containing amphiphilic compounds such as HEUR thickeners.

More preferably, said dispersant is at least one separate molecule component that is surface-active. Preferred separate surface-active molecule components are:
  (i) multi-aziridine compounds as defined above containing functional groups such as sulphonate, sulphate, phosphate and/or phosphonate functional groups, preferably sulphonate and/or phosphonate groups, more preferably sulphonate groups, and/or
  (ii) a polymer preferably having a number average molecular weight as measured with MALDI-ToF-MS as described below of at least 2000 Daltons, more preferably at least 2500 Daltons, more preferably at least 3000 Daltons, more preferably at least 3500 Daltons, more preferably at least 4000 Daltons, and preferably at most 1000000 Daltons, more preferably at most 100000, at most 10000 Daltons.

More preferred separate surface-active molecule components are polymers having a number average molecular weight as measured with MALDI-ToF-MS as described below of at least 2000 Daltons, more preferably at least 2500 Daltons, more preferably at least 3000 Daltons, more preferably at least 3500 Daltons, more preferably at least 4000 Daltons, and preferably at most 1000000 Daltons, more preferably at most 100000, even more preferably at most 10000 Daltons. Preferred polymers are polyethers, more preferably polyether copolymers, even more preferably polyether block copolymers, even more preferably poly (alkylene oxide) block copolymers, even more preferably poly(ethylene oxide)-co-poly(propylene oxide) block copolymers. Non-limited examples of preferred separate surface-active molecule dispersants are Atlas™ G-5002L-LQ obtainable from Croda, Maxemul™ 7101 from Croda and/or Pluronic® P84 from BASF. The amount of separate surface-active molecule component is generally in the range of from 0.1 to 20 wt. %, preferably at least 0.5, more preferably at least 1, even more preferably at least 2, even more preferably at least 3 wt. %, based on the total weight of the aqueous dispersion.

Multi-aziridine compounds as defined under (i) containing functional groups such as sulphonate, sulphate, phosphate and/or phosphonate functional groups, preferably containing sulphonate functional groups, are preferably obtained by reacting part of the isocyanate groups of the polyisocyanates used to prepare the multi-aziridine compound with a hydroxy or amine functional ionic building block (preferably neutralized with an inorganic base). Examples of hydroxy or amine functional ionic building blocks include 2-(cyclohexylamino)ethanesulfonic acid, 3-cyclohexyl-amino)propanesulfonic acid, methyltaurine, taurine, Tegomer® DS-3404. Preferably sulfonic acid salts are used as hydroxy or amine functional ionic building block.

Crosslinking efficiency of a crosslinker can be assessed by assessing the chemical resistance defined and determined as described below.

Storage stability of an aqueous dispersion according to the invention can be assessed by storing the aqueous dispersion in particular at increased temperature, e.g. 50° C., and assessing the change of viscosity, defined and determined as described below, of the stored aqueous dispersion and/or assessing the change of the chemical resistance, defined and determined as described below, in particular the ethanol resistance, of the stored aqueous dispersion.

The aqueous dispersion of the present invention preferably has a storage stability of at least 1 week, preferably at least 2 weeks, more preferably at least 3 weeks and even more preferably at least 4 weeks at 50° C. Storage stable for at least x week(s) at 50° C. means that after the dispersion has been stored for x week at 50° C. (i) the end viscosity of the aqueous dispersion is at most 50 times higher than the starting viscosity, preferably at most 45 times higher than the starting viscosity, more preferably at most 40 times higher than the starting viscosity, more preferably at most 35 times higher than the starting viscosity, more preferably at most 30 times higher than the starting viscosity, more preferably at most 25 times higher than the starting viscosity, more preferably at most 20 times higher than the starting viscosity, more preferably at most 15 times higher than the starting viscosity, more preferably at most 10 times higher than the starting viscosity and most preferably at most 5 times higher than the starting viscosity and/or (ii) the chemical resistance, defined and determined as described below, of the aqueous dispersion decreases with at most 3 points, preferably with at most 2 points, and even more preferably with at most 1 point. Preferably, storage stable for at least x week(s) at 50° C. means that after the dispersion has been stored for x week at 50° C. (i) the end viscosity of the aqueous dispersion is at most 50 times higher than the starting viscosity, preferably at most 45 times higher than the starting viscosity, more preferably at most 40 times higher than the starting viscosity, more preferably at most 35 times higher than the starting viscosity, more preferably at most 30 times higher than the starting viscosity, more preferably at most 25 times higher than the starting viscosity, more preferably at most 20 times higher than the starting viscosity, more preferably at most 15 times higher than the starting viscosity, more preferably at most 10 times higher than the starting viscosity and most preferably at most 5 times higher than the starting viscosity and (ii) the chemical resistance, defined and determined as described below, of the aqueous dispersion decreases with at most 3 points, preferably with at most 2 points, and even more preferably with at most 1 point.

By 'starting viscosity' of an aqueous dispersion is meant the viscosity (defined and determined as described below) of the aqueous dispersion determined upon its preparation and just before the aqueous dispersion is stored at 50° C. By 'end viscosity' of an aqueous dispersion is meant the viscosity (defined and determined as described below) of the aqueous dispersion determined after the aqueous dispersion was stored for x weeks at 50° C.

The aqueous dispersion of the invention can be obtained by dispersing the multi-aziridine compound into water and adjusting the pH of the aqueous dispersion to the desired value or by dispersing the multi-aziridine compound into a mixture of water and at least one base which mixture has a pH such as to obtain an aqueous dispersion with the desired pH value. Dispersing of the multi-aziridine in water or into a mixture of water and at least one base can be done using techniques well-known in the art. Solvents and/or high shear can be utilized in order to assist in the dispersion of the multi-aziridine compound.

The present invention further relates to a process for preparing the aqueous dispersion according to the invention, wherein the process comprises dispersing the multi-aziridine compound as defined herein into water to obtain an aqueous dispersion and adjusting the pH of the aqueous dispersion to the desired value or preferably wherein the process comprises dispersing the multi-aziridine compound as defined herein into a mixture of water and at least one base which mixture has a pH such as to obtain an aqueous dispersion with the desired pH value.

In a preferred embodiment of the invention, the dispersant is a separate surface-active polymer having a number average molecular weight of at least 2000 Daltons (ii). In this preferred embodiment, the process for preparing the aqueous dispersion according to the invention preferably comprises A) optionally but preferably mixing the multi-aziridine compound as defined above in an organic solvent,
B) mixing the multi-aziridine compound as defined above or the solution obtained in step A) with a dispersant as described above to obtain a composition comprising the multi-aziridine compound and dispersant,
C) mixing water and base or mixing basic aqueous medium into said composition comprising the multi-aziridine compound and dispersant, to obtain a dispersion
D) optionally, but preferably, evaporating organic solvent from said dispersion to obtain a further dispersion, and optionally mixing additional water or basic aqueous medium into said further dispersion, to obtain the aqueous dispersion of the present invention.

Step C) is preferably effected using a high-shear dispersion equipment

The present invention further relates to the use of the aqueous dispersion according to the invention for crosslinking a carboxylic acid functional polymer dissolved and/or dispersed, preferably dispersed, in water whereby the amounts of aziridinyl groups and of carboxylic acid groups are chosen such that the stoichiometric amount (SA) of aziridinyl groups on carboxylic acid groups is from 0.1 to 2.0, more preferably from 0.2 to 1.5, even more preferably from 0.25 to 0.95, most preferably from 0.3 to 0.8. The carboxylic acid functional polymer contains carboxylic acid groups and/or carboxylate groups which are preferably free of a covalent bond that blocks these groups to chemically react with the aziridine moiety present in the multi-aziridine compound. As used herein, the amount of carboxylic acid groups present in the carboxylic acid functional polymer is the summed amount of deprotonated and protonated carboxylic acid groups present in the polymer to be crosslinked. The polymer to be crosslinked preferably comprises carboxylate groups which are at least partially neutralized with base. Preferably at least part of the base is a volatile base. Preferably, at least a part of the carboxylic acid groups present in the carboxylic acid functional polymer to be crosslinked are subjected to deprotonation to obtain carboxylate groups. The deprotonation is effected by neutralizing the carboxylic acid functional polymer with a base. Examples of suitable bases are ammonia, secondary amines, tertiary amines, LiOH, NaOH and/or KOH. Examples of secondary amines and tertiary amines are described above. Preferred bases are tertiary amines. Preferred tertiary amines are as described above. Most preferred is triethylamine.

The present invention further relates to an aqueous coating composition comprising a multi-aziridine compound and a carboxylic-acid functional polymer, wherein the composition is an aqueous dispersion having a pH ranging from 8 to 14 and comprises at least two dispersed phases with different composition, wherein the first dispersed phase comprises particles X which particles X comprise a multi-aziridine compound as defined herein, and the second dispersed phase comprises particles Y which particles Y comprise carboxylic acid functional polymer crosslinkable with the multi-aziridine compound as defined herein, with the proviso that particles X neither comprise carboxylic-acid functional polymer nor other compounds crosslinkable with the multi-aziridine compound as defined herein and particles Y neither comprise multi-aziridine compound nor other compounds crosslinkable with the carboxylic acid functionality of the carboxylic acid functional polymer. The coating composition of the invention may further comprise particles comprising multi-aziridine compound and carboxylic-acid functional polymer. Such particles can arise from the coagulation of particles X and particles Y.

The aqueous coating compositions of the invention are preferably self-crosslinkable coating compositions. Self-crosslinkable coating compositions are crosslinkable without the requirement for added compounds which react with groups on the crosslinkable polymer and/or without having to apply heat, although such external triggers can still be employed if desired. It has surprisingly been found that the aqueous coating composition of the present invention has prolonged storage-stability, while at the same time also result in good crosslinking efficiency upon drying of the aqueous coating composition. The compositions according to the invention shows efficient crosslinking reaction at room temperature. The compositions of the invention are also easy to use, providing a one-pot solution for facile storage, handling and application. Accordingly, the aqueous coating compositions according to the invention can provide self-crosslinkable compositions which can be applied as one-pack coating systems without the necessity of mixing reactive materials just prior to application as in a two-pack coating system. The stability of the coating composition of the invention and the improved properties of the corresponding dried film, combined with a favorable hazard profile, generate a high-performance 1K system. This 1K system, wherein crosslinking is triggered only upon coating application, is very accessible to a range of coating applicators, since it reduces handling of hazardous materials and provide good coating properties.

The pH of the coating composition is at least 8. For further prolonging the shelf-life of the coating composition of the invention, it is beneficial that the pH is at least 8.5, preferably at least 9, more preferably at least 9.5. The pH of the coating composition is at most 14, preferably at most 13, more preferably at most 12, even more preferably at most 11.5 and even more preferably at most 11, since this allows to lower the amount of base present in the coating composition of the invention while the shelf life of the coating composition remains sufficiently long. Most preferably, the pH of the coating composition is in the range from 9.5 to 11.5.

The coating composition preferably comprises ammonia, a secondary amine, a tertiary amine, LiOH, NaOH and/or KOH to adjust the pH to the desired value. Preferred amines are ammonia, secondary amines and/or tertiary amines. Examples of such secondary amines are, but not limited to, diisopropylamine, di-sec-butylamine and di-t-butylamine. More preferred amines are tertiary amines. Examples of such tertiary amines are, but not limited to, n-ethylmorpholine, n-methyl piperidine, n,n-dimethyl butyl amine, dimethyl isopropyl amine, dimethyl n-propyl amine, dimethyl ethylamine, triethylamine, dimethyl benzyl amine, n,n-dimethyl ethanolamine, 2-(diethylamino)ethanol, n,n-dimethyl isopropanol amine, 1-dimethylamino-2-propanol, 3-dimethylamino-1-propanol, 2-(dimethylamino)ethanol, 2-[2-(dimethylamino)ethoxy] ethanol. Preferred tertiary amines are n-ethylmorpholine, n-methyl piperidine, n,n-dimethyl butyl amine, dimethyl isopropyl amine, dimethyl n-propyl amine, dimethyl ethylamine, triethylamine and/or dimethyl benzyl amine. Most preferred is triethylamine.

The amount of water in the coating composition is preferably at least 15 wt. %, more preferably at least 20 wt. %, more preferably at least 30 wt. %, even more preferably at least 40 wt. %, on the total weight of the coating composition. The amount of water in the coating composition is preferably at most 90 wt. %, preferably at most 85 wt. %, more preferably at most 80 wt. %, even more preferably at most 70 wt. %, even more preferably at most 60 wt. %, on the total weight of the a coating composition.

The multi-aziridine compound as defined herein is present in the coating composition in an amount of preferably at least 0.5 wt. %, more preferably at least 1 wt. %, more preferably at least 1.5 wt. %, more preferably at least 2 wt. %, even more preferably at least 3 wt. %, even more preferably at least 4 wt. %, even more preferably at least 5 wt. %, even more preferably at least 7 wt. %, on the total solids content of the coating composition. The multi-aziridine compound as defined herein is present in the coating composition in an amount of preferably at most 50 wt. %, preferably at most 30 wt. %, more preferably at most 20 wt. %, more preferably at most 15 wt. %, even more preferably at most 12 wt. %, on the total solids content of the coating composition.

The solids content of the coating composition of the invention is preferably in the range of from 5 to 65 wt. %. The solids content of the coating composition of the invention is more preferably at least 10, even more preferably at least 20, even more preferably at least 25, even more preferably at least 35, and at most 55, even more preferably at most 50 and even more preferably at most 45 wt. %.

At least 50 wt. %, preferably at least 85 wt. %, more preferably at least 95 wt. %, even more preferably at least 99 wt. % of the multi-aziridine compound as defined herein is present in the coating composition in dispersed form. Accordingly, the coating composition of the invention comprises particles X of the multi-aziridine compound as defined herein. Said particles X preferably have a scatter intensity based average hydrodynamic diameter from 30 to 500 nanometer, more preferably from 50 to 350 nm, even more preferably from 110 to 275 nm. The coating composition further comprises particles comprising carboxylic acid functional polymer crosslinkable with the multi-aziridine compound as defined herein. Said particles comprising carboxylic acid functional polymer preferably have a scatter intensity based average hydrodynamic diameter from 30 to 30000 nanometer, more preferably from 40 to 10000 nm, even more preferably from 40 to 3000 nanometer, even more preferably from 40 to 500 nm, even more preferably from 60 to 260 nm.

The carboxylic acid functional polymer is preferably as defined herein above.

The acid value of the carboxylic acid functional polymer is preferably from 2 to 135 mg KOH/gram of the carboxylic acid functional polymer, more preferably from 3 to 70 mg KOH/g carboxylic acid functional polymer, even more preferably from 10 to 50 mg KOH/g carboxylic acid functional polymer and even more preferably from 15 to 50 mg KOH/g carboxylic acid functional polymer. In case high crosslink density is required, the acid value of the carboxylic acid functional polymer is preferably from 50 to 200 mg KOH/g carboxylic acid functional polymer. As used herein, the acid value of the carboxylic acid functional polymer(s) is calculated according to the formula AV=((total molar amount of carboxylic acid components included in the carboxylic acid functional polymer(s) per gram of total amount of components included in the carboxylic acid functional polymer(s))*56.1*1000) and is denoted as mg KOH/gram carboxylic acid functional polymer(s). The acid value of the carboxylic acid functional polymer(s) can thus be controlled by the molar amount of carboxylic acid components that is used to prepare the carboxylic acid functional polymer(s). In case the acid value cannot be properly calculated, the acid value is determined by ASTM D1639-90(1996)e1.

The ratio of number-average molecular weight $M_n$ of the carboxylic acid functional polymer to acid value of the carboxylic acid functional polymer is preferably at least 150, more preferably at least 300, even more preferably at least 600, even more preferably at least 1000, even more preferably at least 5000 and most preferably at least 15000. As used herein, the number-average molecular weight $M_n$ of the carboxylic acid functional polymer is determined by Size Exclusion Chromatography with NMP-MEK.

The coating composition comprises at least one carboxylic acid functional polymer. The coating composition may comprise a blend of different carboxylic acid functional polymers. The carboxylic acid functional polymers contain carboxylic acid groups and/or carboxylate groups which are preferably free of a covalent bond that blocks these groups to chemically react with the aziridine moiety present in the multi-aziridine compound. As used herein, the amount of carboxylic acid groups present in the carboxylic acid functional polymer is the summed amount of deprotonated and protonated carboxylic acid groups present in the polymer to be crosslinked. The polymer to be crosslinked preferably comprises carboxylate groups which are at least partially neutralized with base. Preferably at least part of the base is a volatile base. Preferably, at least a part of the carboxylic acid groups present in the carboxylic acid functional polymer to be crosslinked are subjected to deprotonation to obtain carboxylate groups. The deprotonation is effected by neutralizing the carboxylic acid functional polymer with a base. Examples of suitable bases are ammonia, secondary amines, tertiary amines, LiOH, NaOH and/or KOH. Examples of secondary amines and tertiary amines are described above. Preferred bases are tertiary amines. Preferred tertiary amines are as described above. Most preferred is triethylamine.

The coating composition of the invention preferably comprises carboxylic acid functional polymer in an amount of at least 3 wt. %, preferably at least 5 wt. %, more preferably at least 10 wt. %, more preferably at least 20 wt. %, even more preferably at least 30 wt. %, even more preferably at least 40 wt. %, even more preferably at least 50 wt. %, on the total weight of the aqueous dispersion. The coating composition of the invention preferably comprises carboxylic acid functional polymer in an amount of at most 60 wt. %, preferably at most 55 wt. %, on the total weight of the aqueous dispersion.

Preferably, the amounts of aziridinyl groups and of carboxylic acid groups are chosen such that the stoichiometric amount (SA) of aziridinyl groups on carboxylic acid groups is from 0.1 to 2.0, more preferably from 0.2 to 1.5, even more preferably from 0.25 to 0.95, most preferably from 0.3 to 0.8.

The coating composition of the invention can be obtained by (i) dispersing the multi-aziridine compound into water and adjusting the pH of the aqueous dispersion to the desired value or by dispersing the multi-aziridine compound into a mixture of water and at least one base which mixture has a pH such as to obtain an aqueous dispersion with the desired pH value, and (ii) mixing the aqueous dispersion obtained in step (i) with an aqueous dispersion of the carboxylic acid functional polymer. Dispersing of the multi-aziridine in water or into a mixture of water and at least one base can be done using techniques well-known in the art. Solvents and/or high shear can be utilized in order to assist in the dispersion of the multi-aziridine compound.

Alternatively, the multi-aziridine compound can be self-dispersing in which case it can directly be added to the carboxylic acid functional polymer to form separate particles. The multiaziridine can become self-dispersing by incorporating ionic groups, polar non-ionic groups such as polyalkylene oxides or any combination thereof.

The coating composition may further comprise organic solvent in an amount of at most 35 wt. %, preferably at most 30, for example at most 25, for example at most 20, for example at most 12, for example at most 10, for example at most 8, for example at most 5, for example at most 4, for example at most 3, for example at most 2, for example at most 1, for example at most 0.5, for example at most 0.2, for example at most 0.1 wt % on the total weight of the coating composition. Organic solvent may optionally be added before, during and/or after synthesis of the multi-aziridine(s). Organic solvent can be utilized in order to assist in dispersing the multi-aziridine compound in water. If desired, organic solvent can be removed afterwards from the crosslinker composition by reduced pressure and/or increased temperatures. Typical organic solvents are glycols, ethers, alcohols, cyclic carbonates, pyrrolidones, dimethylsulfoxide, n-formylmorpholine, amides and ketones. Preferred solvents are glycols (including glycol ethers), ethers, alcohols, cyclic carbonates and ketones.

Preferably the dispersing of the multi-aziridine compound is done in the presence of a dispersant. Accordingly, the coating composition of the invention preferably comprises a dispersant. In the context of the present invention, a dispersant is a substance that promotes the formation and colloidal stabilisation of a dispersion. In the present invention, said dispersant is preferably a species that is non-covalently attached to the multi-aziridine compound and/or said dispersant is a separate molecule component that is surface-active. Examples of species non-covalently attached to the multi-aziridine compound are urethane and/or urea containing amphiphilic compounds such as HEUR thickeners.

More preferably, said dispersant is at least one separate molecule component that is surface-active. Preferred dispersants are as described above.

The present invention further relates to a process for preparing the coating composition according to the invention, wherein the process comprises (i) dispersing the multi-aziridine compound as defined herein above into water to obtain an aqueous dispersion and adjusting the pH of the aqueous dispersion to a desired value or the process comprises dispersing the multi-aziridine compound as defined in herein above into a mixture of water and at least one base which mixture has a pH such as to obtain an aqueous dispersion with a desired pH value, and (ii) mixing the aqueous dispersion obtained in step (i) with an aqueous dispersion of the carboxylic acid functional polymer. Preferably, the process comprises mixing basic aqueous medium into the multi-aziridine compound as defined herein above, whereby the pH of the basic aqueous medium is chosen such as to obtain a coating composition with the desired pH value.

The process for preparing the coating composition of the invention preferably comprises
A) optionally, but preferably, mixing the multi-aziridine compound as defined herein above in an organic solvent,
B) mixing the multi-aziridine compound as defined herein above or the solution obtained in step A) with a dispersant to obtain a composition comprising the multi-aziridine compound and dispersant,
C) mixing water and base or mixing basic aqueous medium into said composition comprising the multi-aziridine compound and dispersant, to obtain a dispersion
D) optionally, but preferably, evaporating organic solvent from said dispersion to obtain a further dispersion, and optionally mixing additional water or basic aqueous medium into said further dispersion, to obtain an aqueous dispersion of the multi-aziridine compound, and
E) mixing the aqueous dispersion of the multi-aziridine compound obtained in step D) with an aqueous dispersion of the carboxylic acid functional polymer, to obtain the coating composition of the invention.

Step C) is preferably effected using a high-shear dispersion equipment.

The present invention further relates to a substrate having a coating obtained by (i) applying a coating composition as described above to a substrate and (ii) drying the coating composition by evaporation of volatiles. The drying of the coating composition is preferably effected at a temperature lower than 160° C., preferably at a temperature lower than 90° C., more preferably at a temperature lower than 50° C. and most preferably at ambient temperature. The coating composition according to the invention can be applied to any kind of substrate, such as for example wood, leather, concrete, textile, plastic, vinyl floors, glass, metal, ceramics, paper, wood plastic composite, glass fiber reinforced materials. The thickness of the dry coating on the substrate is preferably from 1 to 200 micron, more preferably from 5 to 150 micron and most preferably from 15 to 90 microns. In case the coating composition is an ink composition, the thickness of the dry ink is preferably from 0.005 to 35 micron, more preferably from 0.05 to 25 micron and most preferably from 4 to 15 microns.

The invention is further defined by the set of exemplary embodiments as listed hereafter. Any one of the embodiments, aspects and preferred features or ranges as disclosed in this application may be combined in any combination, unless otherwise stated herein or if technically clearly not feasible to a skilled person.

[1] A multi-aziridine compound having:
a) at least 2 of the following structural units (A):

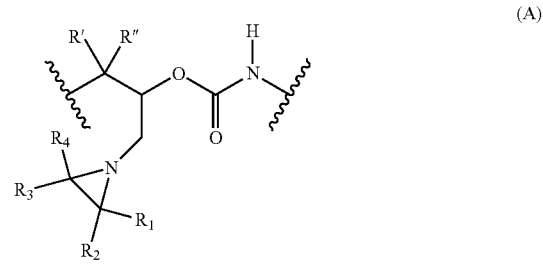

whereby
$R_1$ is H;
$R_2$ and $R_4$ are independently chosen from H, a linear group containing from 1 to 8 carbon atoms and optionally containing one or more heteroatoms, a branched or cyclic group containing from 3 to 8 carbon atoms and optionally containing one or more heteroatoms, phenyl, benzyl, or pyridinyl;
$R_3$ is chosen from a linear group containing from 1 to 8 carbon atoms and optionally containing one or more heteroatoms, a branched or cyclic group containing from 3 to 8 carbon atoms and optionally containing one or more heteroatoms, phenyl, benzyl, or pyridinyl;
or $R_2$ and $R_3$ (in case $R_2$ is different than H) may be part of the same cyclic group containing from 3 to 8 carbon atoms;
R' and R" are independently H or an aliphatic hydrocarbon group containing from 1 to 12 carbon atoms; and
b) a molecular weight of at least 600 Daltons and of at most 20000 Daltons, wherein the molecular weight is determined using MALDI-TOF mass spectrometry according to the description; and
the multi-aziridine compound is obtained by reacting at least a polyisocyanate and a compound (B) with the following structural formula:

whereby n is an integer equal to or larger than 2, Z is an n-valent radical or a mixture of n-valent radicals and D has the following structural formula:

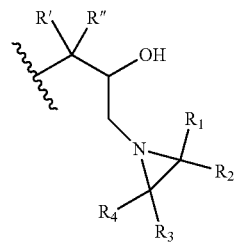

whereby the molar ratio of moiety D to isocyanate moieties on polyisocyanates is from 0.5 to 2.

[2] The multi-aziridine compound according to embodiment [1], wherein $R_2$ and $R_4$ are independently chosen from H or an aliphatic hydrocarbon group containing from 1 to 2 carbon atoms, and $R_3$ is an aliphatic hydrocarbon group containing from 1 to 4 carbon atoms.

[3] The multi-aziridine compound according to any of the preceding embodiments, wherein $R_2$ is H, $R_3$ is $CH_3$ and $R_4$ is H.

[4] The multi-aziridine compound according to any of the preceding embodiments, wherein R' and R" are H.

[5] The multi-aziridine compound according to any of the preceding embodiments, wherein the multi-aziridine compound contains 2 to 10 structural units (A).

[6] The multi-aziridine compound according to any of the preceding embodiments, wherein the multi-aziridine compound contains 2 to 4 structural units (A).

[7] The multi-aziridine compound according to any of the preceding embodiments, characterized in that the multi-aziridine compound has a molecular weight from 600 to 200000 Daltons, more preferably the multi-aziridine compound has a molecular weight of at least 800 Daltons, even more preferably at least 840 Daltons, even more preferably at least 1000 Daltons and preferably at most 20000 Daltons, more preferably at most 10000 Daltons, more preferably at most 5000 Daltons, wherein the molecular weight is determined using MALDI-TOF mass spectrometry according to the description.

[8] The multi-aziridine compound according to any of the preceding embodiments, wherein the multi-aziridine compound is obtained by reacting at least a polyisocyanate and a compound (B) with the following structural formula:

Whereby n is an integer equal to or larger than 2, Z is an n-valent radical or a mixture of n-valent radicals and D has the following structural formula:

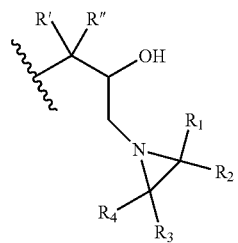

whereby the molar ratio of moiety D to isocyanate moieties on polyisocyanates is from 0.5 to 2, and whereby R', R", $R_1$, $R_2$, $R_3$ and $R_4$ are defined as in any of preceding embodiments.

[9] The multi-aziridine compound according to embodiment [8], wherein Z is an n-valent radical consisting of a collection of atoms covalently connected in linear or branched configuration, which collection of atoms consists of i) carbon and hydrogen atoms, ii) carbon, hydrogen and oxygen atoms, iii) carbon, hydrogen and nitrogen atoms, or iv) carbon, hydrogen, oxygen and nitrogen atoms, or wherein Z is a mixture of such n-valent radicals.

[10] The multi-aziridine compound according to embodiment [8] or [9], wherein the polyisocyanate is a diisocyanate.

[11] The multi-aziridine compound according to embodiment [8] to [10], wherein the Z is a divalent radical (n=2) and Z—[D]$_n$ is according to the following formula:

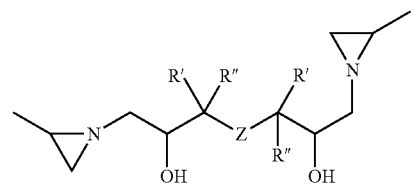

[12] The multi-aziridine compound according to embodiment [10] or [11], wherein the diisocyanate is selected from the group consisting of 1,5-pentamethylene diisocyanate, 1,6-hexamethylene diisocyanate, isophorone diisocyanate, 4,4'-dicyclohexyl methane diisocyanate, 2,2,4-trimethyl hexamethylene diisocyanate, 2,4,4-trimethyl hexamethylene diisocyanate, tetramethylxylene diisocyanate (all isomers) and any mixture thereof.

[13] The multi-aziridine compound according to any of embodiments [13] to [17], wherein compound (B) is obtained by reacting at least an n-functional polyepoxide (wherein n is defined as in any of preceding embodiments compound with an aziridine with the following structural formula:

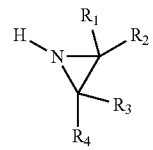

whereby $R_1$, $R_2$, $R_3$ and $R_4$ are defined as in any of the preceding embodiments.

[14] The multi-aziridine compound according to any of the preceding embodiments, wherein the n-functional polyepoxide is a difunctional polyepoxide compound.

[15] The multi-aziridine compound according to any of the preceding embodiments, wherein the n-functional polyepoxide is selected from the group consisting of Bisphenol A diglycidyl ether (CAS 1675-54-3), Hydrogenated Bisphenol A diglycidyl ether (CAS 30583-72-3), Neopentyl glycol diglycidyl ether (CAS 17557-23-2), butanediol diglycidyl ether (CAS 2425-79-8), ethylene glycol diglycidyl ether (CAS 2224-15-9), 1,6-Hexanediol diglycidyl ether (CAS 16096-31-4), polypropyleneglycol diglycidyl ether (CAS 26142-30-3), Poly(ethylene glycol) diglycidyl ether (CAS 72207-80-8) and any mixture thereof.

[16] A crosslinker composition comprising at least one multi-aziridine compound according to any of the preceding embodiments and further comprising at least one additional component.

[17] The crosslinker composition according to embodiment [16], wherein the amount of aziridinyl group functional molecules having a molecular weight lower than 580 Daltons is lower than 5 wt. %, relative to the total weight of the crosslinker composition, whereby the molecular weight is determined using LC-MS as described in the description.

[18] The crosslinker composition according to any of embodiments [16] or [17], wherein the crosslinker composition is an aqueous dispersion comprising particles of the multi-aziridine compound according to any of embodiments [1] to [15].

[19] The crosslinker composition according to embodiment [18], wherein the particles present in the dispersion have a scatter intensity based average hydrodynamic diameter from 5 to 700 nanometer, more preferably from 10 to 300 nm, even more preferably from 15 to 200 nm, most preferably 15 to 150 nm, wherein the scatter intensity based average hydrodynamic diameter is determined as described in the description.

[20] The crosslinker composition according to any of embodiments [18] to [19], wherein the aqueous dispersion has a pH of at least 8.8, more preferably at least 10 and most preferably at least 10.5.

[21] The crosslinker composition according to any of embodiments [18] to [20], wherein the aqueous dispersion has a pH lower than 12, preferably lower than 11.5.

[22] Use of the multi-aziridine compound according to any of embodiments [1] to [15] or the crosslinker composition according to any of embodiments [16] to [21] for crosslinking a carboxylic acid functional polymer dissolved and/or dispersed in an aqueous medium.

[23] A two-component system comprising a first component and a second component each of which is separate and distinct from each other and wherein the first component comprises a carboxylic acid functional polymer dissolved and/or dispersed in an aqueous medium and the second component comprises a multi-aziridine compound according to any of embodiments [1] to [15] or the crosslinker composition according to any of embodiments [16] to [21].

[24] A substrate having a coating obtained by (i) applying a coating composition obtained by mixing the first and second component of the two-component system according to embodiment [23] to a substrate and (ii) drying the coating composition by evaporation of volatiles.

[25] An aqueous coating composition comprising dispersed particles comprising the multi-aziridine compound according to any one of embodiments [1] to [15], and carboxylic-acid functional polymer particles, and having a pH ranging from 8 to 14.

[26] The aqueous coating composition according to embodiment [25], characterized in that the amounts of aziridinyl groups and of carboxylic acid groups are chosen such that the stoichiometric amount (SA) of aziridinyl groups on carboxylic acid groups is from 0.1 to 2.0, more preferably from 0.2 to 1.5, even more preferably from 0.25 to 0.95, most preferably from 0.3 to 0.8.

[27] The aqueous coating composition according to embodiment [25] to [26], characterized in that the solids content of the coating composition is at least 5, preferably at least 10, even more preferably at least 20, even more preferably at least 25, even more preferably at least 35 and at most 55, more preferably at most 50 and even more preferably at most 45 wt. %.

[28] The aqueous coating composition according to any of embodiments [25] to [27], characterized in that the carboxylic acid functional polymer is selected from the group consisting of vinyl polymers, polyacrylates, polymethacrylates, poly(acrylate-co-methacrylate)s and mixtures thereof.

[29] The aqueous coating composition according to any of embodiments [25] to [28], characterized in that the carboxylic acid functional polymer is selected from the group consisting of polyurethanes, poly(urethane-co-acrylate)s, poly(urethane-co-methacrylate)s, poly(urethane-co-acrylate-co-methacrylate), polyureas, and mixtures thereof.

[30] The aqueous coating composition according to any of embodiments [25] to [29], characterized in that the carboxylic acid functional polymer has an acid value of from 2 to 135 mg KOH/gram of the carboxylic acid functional polymer, more preferably from 3 to 70 mg KOH/g carboxylic acid functional polymer, even more preferably from 10 to 50 mg KOH/g carboxylic acid functional polymer and even more preferably from 15 to 50 mg KOH/g carboxylic acid functional polymer.

[31] The aqueous coating composition according to any of embodiments [25] to [30], characterized in that the aqueous coating composition is self-crosslinkable.

[32] The aqueous coating composition according to any of embodiments [25] to [31], wherein the aqueous coating composition comprises at least two dispersed phases with different composition, wherein the first dispersed phase comprises particles X which particles X comprise said multi-aziridine compound, and the second dispersed phase comprises particles Y which particles Y comprise carboxylic acid functional polymer crosslinkable with said multi-aziridine compound, wherein the particles X neither comprise carboxylic-acid functional polymer nor other compounds crosslinkable with said multi-aziridine compound and particles Y does not comprise said multi-aziridine compound, preferably particles Y neither comprise said multi-aziridine compound nor other crosslinking compounds able to crosslink the carboxylic acid functionality of the carboxylic acid functional polymer, more preferably particles Y neither comprise said multi-aziridine compound nor other crosslinking compounds.

Particle Size Measurement

The scatter intensity based average hydrodynamic diameter of the particles was determined using a method derived from the ISO 22412:2017 standard with a Malvern Zetasizer Nano S90 DLS instrument that was operated under the following settings: as material, a polystyrene latex was defined with a RI of 1.590 and an absorption of 0.10 with a continuous medium of demineralized water with a viscosity of 0.8812 cP and a RI of 1.332 at 25° C. Measurements were performed in DTS0012 disposable cuvettes, obtained from Malvern Instruments (Malvern, Worcestershire, United Kingdom). Measurements were performed under a 173° backscatter angle as an average of 3 measurements after 120 seconds equilibration, consisting of 10-15 subruns—optimized by the machine itself. The focus point of the laser was at a fixed position of 4.65 cm and data was analyzed using a general-purpose data fitting process. Samples were prepared by diluting 0.05 g (1 droplet) sample dispersion in approximately 5 mL of demineralized water. If the sample still looked hazy it was further diluted with distilled water until it becomes almost clear. This method is suitable for determining particle sizes from 2 nm to 3 μm.

pH Measurement

The pH of a sample is determined based on the ISO 976:2013 standard. Samples are measured at 23° C. using a Metrohm 691 pH-meter equipped with combined glass electrode and PT-1000 temperature sensor. The pH-meter is calibrated using buffer solutions of pH 7.00 and 9.21 prior to use.

NCO Determination

The NCO content of a sample is determined based on the ASTM D2572-19 standard. In the procedure, the sample is reacted with excess n-dibutylamine. The excess of n-dibutylamine is subsequently back-titrated with standard 1 N hydrochloric acid (HCl). The difference in titration volume between the sample and a blank is the measure of the isocyanate content on solids, according to the following formula: % $NCO_{solids}=[(Vb-Vm)*N*4.2]/(A*s/100)$, where % $NCO_{solids}$ is the isocyanate content on solids, Vb is the volume of HCl used in the blank, Vm is the volume of HCl used in the sample, N is the normality of the HCl solution, A is the sample weight in grams and s is the solids content of the sample in %. Measurements are performed in duplicate using a potentiometric endpoint on a Metrohm 702SM Titrino titrator (accepting the measurement if the difference between duplicates is <0.1%$_{NCO}$).

AV Determination

The acid value on solid material (AV) of a sample is determined based on the ASTM D1639-90(1996)e1 standard. In the procedure, the sample, dissolved in a good solvent, is titrated with alcoholic potassium hydroxide solution of a known concentration (KOH). The difference in titration volume between the sample and a blank is the measure of the acid value on solids, according to the following formula: AV=[(Vblank-Vsample)*$N_{KOH}$*56.1]/(W*S/100), where AV is acid number on solids in mg KOH/g solid material, Vblank is the volume of KOH solution used in the blank, Vsample is the volume of KOH solution used in the sample, $N_{KOH}$ is the normality of the KOH solution, W is the sample weight in grams and S is the solids content of the sample in %. Measurements are performed in duplicate using a potentiometric endpoint on a Metrohm 702SM Titrino titrator (accepting the measurement if the difference between duplicates is <0.1 mg KOH/g solid material).

Chemical Resistance

Chemical resistance testing based on DIN 68861-1:2011-01 standard.

Unless indicated otherwise the chemical resistance is tested as follows:

Coating compositions are composed at 0.9 stoichiometric amounts (SA) of total carboxylic acid-reactive functional groups (e.g. aziridine) compared to carboxylic acid functional groups. Coating compositions are treated as described in the examples, and then cast at 100 μm wet layer thickness using a wire bar applicator. After casting, films were dried for 1 hour at 25° C., then annealed at 50° C. for 16 hours. Subsequently, a piece of cotton wool was soaked in 1:1 Ethanol: demineralized water (by weight) and placed on the film for 60 minutes (unless indicated otherwise). After removal of the cotton wool and overnight recovery, the spots were scored according to the following ranks:

1 Complete coating degradation
2 Structural damage to the coating
3 Severe marking on coating, visible from multiple directions
4 Slight marking on coating, visible from specific angles
5 No observed marking or gloss change Viscosity Measurements:

The apparent viscosity is determined according to ISO 2555:2018. The measurement is performed at 23° C. on a Brookfield DVE-LV viscometer (single-cylinder geometry) at 60 rpm. The spindle is selected from S62, S63 or S64, using the lowest numbered spindle (i.e. the largest spindle) that yields a reading between 10% and 100% torque.

Size Exclusion Chromatography with NMP-MEK

The molecular weight distribution is measured with an Alliance Separation Module (Waters e2695), including a pump, autoinjector, degasser, and column oven. The eluent is n-Methyl pyrrolidone (NMP) 80%/methylethylketone 20% (MEK) with the addition of 0.01 M lithium bromide. The injection volume was 150 μl. The flow was established at 1.0 ml/min. Three PL Mixed B (Polymer Laboratories) with a guard column (5 μm PL) were applied at a temperature of 70° C. The detection was performed with a differential refractive index detector (Waters 2414) at 50° C. The samples are dissolved in the eluent using a concentration of 5 mg polymer per mL solvent. The solubility is judged with a laser pen after 24 hours stabilization at room temperature; if any scattering is visible the samples are filtered first. The calculation was performed with eight polystyrene standards (polymer standard services), ranging from 160 to 1,737,000 Dalton. The calculation was performed with Empower software (Waters) with a third order calibration curve. The obtained molar masses are polystyrene equivalent molar masses (Dalton).

$T_g$ Measurement by DSC

The glass transition temperature ($T_g$) of a polymer is measured by Differential Scanning Calorimetry (DSC) at a heating rate of 10° C./min in $N_2$ atmosphere at a flow rate of 50 mL/minute, on a TA Instruments Discovery DSC 250 apparatus according to the following method: a sample of 5±0.5 mg was weighed and placed in the DSC cell at a temperature between 20 and 25° C. The sample was cooled down to -120° C. and equilibrated at that temperature; upon equilibration the sample was heated up from -120° C. up to 160° C. at a heating rate of 5° C./minute; the sample was kept at that temperature for 2 minutes and it was subsequently cooled down to -120° C. at a cooling rate of 20° C./min; once the sample reached -120° C. the temperature was maintained for 5 minutes; subsequently, the sample was heated up from -120° C. up to 220° C. at a heating rate of 5° C./minute (thermograph A). The $T_g$ was measured from this last thermograph (thermograph A) as the half width of the step in the DSC signal (DSC thermograph, Heat Flow vs. Temperature) observed for a $T_g$. The processing of the DSC signal and the determination of the $T_g$ was carried out using TRIOS software package version 5.0 provided by TA instruments.

Low Molecular Weight Fraction by LC-MS

LC system: Agilent 1290 Infinity II; Detector #1: Agilent 1290 Infinity II PDA; Detector #2: Agilent iFunnel 6550 Q-TOF-MS.

LC-MS analysis for the low molecular weight fraction was performed using the following procedure. A solution of ~100 mg/kg of material was prepared gravimetrically in methanol and stirred. 0.5 μl of this solution was injected into a UPLC equipped with ESI-TOF-MS detection. The column used was a 100×2.1 mm, 1.8 um, Waters HSS T3 C18 operated at 40° C. Flow rate was 0.5 ml·min$^{-1}$. Solvents used were 10 mM $NH_4CH_3COO$ in water set to pH 9.0 with $NH_3$ (Eluent A), Acetonitrile (B) and THF (C). Two binary gradients were applied from 80/20 A/B to 1/99 A/B in 10 minutes and from 1/99 A/B to 1/49/50 A/B/C in 5 minutes, after which starting conditions are applied (80/20 A/B). Assuming linear MS response of all components over all response ranges and an equal ionization efficiency for all components, Total Ion Current signals were integrated. In case of coelution extracted ion chromatograms of that particular species were integrated. Dividing the integrated signal of a particular low-molecular weight peak by the total integrated sample signal yields the fraction of that low molecular weight species.

MALDI-ToF-MS

All MALDI-ToF-MS spectra were acquired using a Bruker Ultraflextreme MALDI-ToF mass spectrometer. The instrument is equipped with a Nd:YAG laser emitting at 1064 nm and a collision cell (not used for these samples). Spectra were acquired in the positive-ion mode using the reflectron, using the highest resolution mode providing accurate masses (range 60-7000 m/z). Cesium Tri-iodide (range 0.3-3.5 kDa) was used for mass calibration (calibration method: IAV Molecular Characterisation, code MC-MS-05). The laser energy was 20%. The samples were dissolved in THF at 36 approx. 50 mg/mL. The matrix used was: DCTB (trans-2-[3-(4-tert-Butylphenyl)-2-methyl-2-propenylidene]malononitrile), CAS Number 300364-84-5. The matrix solution was prepared by dissolving 20 mg in 1 mL of THF.

Sodium iodide was used as salt (NaI, CAS Number 7681-82-5); 10 mg was dissolved in 1 ml THF with a drop of MeOH added. Ratio sample:matrix:salt=10:200:10 (µl), after mixing, 0.5 µL was spot on MALDI plate and allowed to air-dry. The peaks measured in the MALDI spectrum are sodium adducts of multi-aziridine compounds, and in the context of this specification the molecular weight (MW) of the multi-aziridine compound corresponds to MW=Obs. $[M+M_{cation}]-M_{cation}$, where Obs. $[M+M_{cation}]$ is the MALDI-TOF MS peak and $M_{cation}$ is the exact mass of the cation used for making the adduct (in this case sodium with $M_{cation}$=23.0 Da). Multi-aziridine compounds can be identified by comparing the MW with the exact molecular mass (i.e. the sum of the—non-isotopically averaged—atomic masses of its constituent atoms) of a theoretical structure, using a maximum deviation of 0.6 Da.

Genotoxicity Testing

Genotoxicity of was evaluated by the ToxTracker® assay (Toxys, Leiden, the Netherlands). The ToxTracker assay is a panel of several validated Green Fluorescent Protein (GFP)-based mouse embryonic stem (mES) reporter cell lines that can be used to identify the biological reactivity and potential carcinogenic properties of newly developed compounds in a single test. This methodology uses a two step-approach.

In the first step a dose range finding was performed using wild-type mES cells (strain B4418). 20 different concentrations for each compound was tested, starting at 10 mM in DMSO as highest concentration and nineteen consecutive 2-fold dilutions.

Next, genotoxicity of was evaluated using specific genes linked to reporter genes for the detection of DNA damage; i.e. Bscl2 (as elucidated by U.S. Pat. No. 9,695,481 B2 and EP2616484B1) and Rtkn (Hendriks et. Al. Toxicol. Sci. 2015, 150, 190-203) biomarkers. Genotoxicity was evaluated at 10, 25 and 50% cytotoxicity in absence and presence of rat S9 liver extract-based metabolizing systems (aroclor1254-induced rats, Moltox, Boone, NC, USA). The independent cell lines were seeded in 96-well cell culture plates, 24 h after seeding the cells in the 96-well plates, fresh ES cell medium containing the diluted test substance was added to the cells. For each tested compound, five concentrations are tested in 2-fold dilutions. The highest sample concentration will induce significant cytotoxicity (50-70%). In case of no or low cytotoxicity, 10 mM or the maximum soluble mixture concentration is used as maximum test concentration. Cytotoxicity is determined by cell count after 24 h exposure using a Guava easyCyte 10HT flow cytometer (Millipore).

GFP reporter induction is always compared to a vehicle control treatment. DMSO concentration is similar in all wells for a particular compound and never exceeds 1%. All compounds were tested in at least three completely independent repeat experiments. Positive reference treatment with cisplatin (DNA damage) were included in all experiments. Metabolic was evaluated by addition of S9 liver extract. Cells are exposed to five concentrations of the test compound in the presence of S9 and required co-factors (RegenSysA+B, Moltox, Boone, NC, USA) for 3 h. After washing, cells are incubated for 24 h in fresh ES cell medium. Induction of the GFP reporters is determined after 24 h exposure using a Guava easyCyte 10HT flow cytometer (Millipore). Only GFP expression in intact single cells is determined. Mean GFP fluorescence and cell concentrations in each well is measured, which is used for cytotoxicity assessment. Data was analyzed using ToxPlot software (Toxys, Leiden, the Netherlands). The induction levels reported are at compound concentrations that induce 10%, 25% and 50% cytotoxicity after 3 h exposure in the presence of S9 rat liver extract and 24 h recovery or alternatively after 24 h exposure when not in the presence of S9 rat liver extract.

A positive induction level of the biomarkers is defined as equal to or higher than a 2-fold induction at at least one of 10, 25 and 50% cytotoxicity in the absence or presence of the metabolizing system rat S9 liver extract; a weakly positive induction as higher than 1.5-fold and lower than 2-fold induction at at least one of 10, 25 and 50% cytotoxicity (but lower than 2-fold at 10, 25 and 50% cytotoxicity) in the absence or presence of the metabolizing system rat S9 liver extract and a negative as lower than or equal to a 1.5-fold induction at 10, 25 and 50% cytotoxicity in the absence and presence of rat S9 liver extract-based metabolizing systems.

Components and Abbreviations Used

Dimethylformamide (CAS No. 68-12-2) was obtained from Acros Organics (a division of Thermo Fisher Scientific).

Di(propylene glycol) dimethyl ether (Proglyde DMM, CAS No. 111109-77-4) was obtained from Dow Inc.

Trimethylolpropane tris(2-methyl-1-aziridinepropionate), CAS No. 64265-57-2, CX-100 was obtained from DSM.

Bisphenol A diglycidyl ether (CAS No. 1675-54-3) was obtained from Tokyo Chemical Industry Co., Ltd.

Neopentyl glycol diglycidyl ether (CAS No. 17557-23-2) was obtained from Sigma-Aldrich.

Potassium carbonate (CAS No. 584-08-7) was obtained from Alfa Aesar (a division of Thermo Fisher Scientific).

2-Methylaziridine (propyleneimine, CAS No. 75-55-8) was obtained from Menadiona S.L. (Palafolls, Spain).

1,3-bis(2-isocyanatopropan-2-yl)benzene (m-tetramethylxylene diisocyanate, TMXDI, CAS No. 2778-42-9) was obtained Allnex.

Bismuth neodecanoate (CAS No. 34364-26-6) obtained from TIB chemicals AG (Mannheim, Germany).

H12MDI (4,4'-Methylenebis(phenyl isocyanate, Desmodur® W, CAS No. 101-66-8) from Covestro.

Maxemul™ 7101 was obtained from Croda.

Methyl ethyl ketone (CAS No. 78-93-3) was obtained from Sigma-Aldrich.

Jeffamine® D-230 (CAS No. 9046-10-0) was obtained from Huntsman

Oxymer™ M112 was obtained from Perstorp.

Cyclohexanol (CAS No. 108-93-0) was obtained from Sigma-Aldrich

Ymer™ N-120 was obtained from Perstorp.

n-methylbutylamine (CAS No. 110-68-9) was obtained from Sigma-Aldrich 3-cyclohexylamino-1-propanesulfonic acid sodium salt (CAS No. 105140-23-6) was obtained from Fluorochem n-butylglycidyl ether (CAS No. 2426-08-6) was obtained from Alfa Aesar (a division of Thermo Fisher Scientific).

Atlas™ G-5002L-LQ was obtained from Croda.

Voranol™ P-400 was obtained from Dow Inc.

Hydrazine (16% solution in water, CAS No. 302-01-2) was obtained from Honeywell.

Dimethylol propionic acid (DMPA, CAS No. 4767-03-7) was obtained from Perstop Polyols.

Triethylamine (TEA, CAS No. 121-44-8) was obtained from Arkema Dibutyltindilaurate (CAS No. 77-58-7) was obtained from Sigma-Aldrich.

Polypropyleneglycol with a number average molecular weight of 1000 Da and with a number average molecular weight of 2000 Da was obtained from BASF.

Sodium lauryl sulphate (30% solution in water, CAS No. 73296-89-6) was obtained from BASF.

Acetone (CAS No. 67-64-1) was obtained from Acros Organics (a division of Thermo Fisher Scientific).

Methyl methacrylate (CAS No. 80-62-6) was obtained from Lucite Int. n-Butyl acrylate (CAS No. 141-32-2) was obtained from Dow Chemical.

Methacrylic acid (CAS No. 79-41-4) was obtained from Lucite Int.

Ammonium persulphate (CAS No. 7727-54-0) was obtained from United Initiators.

Ammonia (25% solution in water, CAS No. 1336-21-6) was obtained from Merck.

1-Butanol (CAS No. 71-36-3) was obtained from Sigma-Aldrich.

PREPARATIVE EXAMPLE 1: SYNTHESIS OF WATERBORNE POLYURETHANE POLYMER P1

A 1 L flask equipped with a thermometer and overhead stirrer was charged with 29.9 grams of dimethylolpropionic acid, 282.1 grams of a polypropylene glycol with an average Mn of 2000 Da (with an OH-value of 55.5 mg KOH/g polymer), 166.5 grams of a polypropylene glycol with an average Mn of 1000 Da (with an OH-value of 110 mg KOH/g polymer) and 262.8 grams of isophorone diisocyanate. The reaction mixture was placed under $N_2$ atmosphere, heated to 50° C. and 0.07 g of dibutyltin dilaurate was added. The mixture was allowed to exotherm and kept at 95° C. for 1 hour. The NCO content of the resultant urethane prepolymer was 7.00% on solids (theoretically 7.44%). The prepolymer was cooled down to 60° C. and TEA (18.7 grams) was added and the resulting mixture was stirred for 30 minutes. A dispersion of the resultant prepolymer was made by feeding this entire prepolymer to a mixture of 1100 grams of demineralized water, 19.5 grams of nonylphenol ethoxylate 9 eo and 4.0 grams of triethylamine at room temperature in 60 minutes. After the feed was completed, the mixture was stirred for 5 minutes and hydrazine (16% solution in water, 111.2 grams) was added. The dispersion was stirred for a further 1 h.

PREPARATIVE EXAMPLE 2: SYNTHESIS OF WATERBORNE ACRYLIC POLYMER A1

A 2 L four-necked flask equipped with a thermometer and overhead stirrer was charged with sodium lauryl sulphate (30% solids in water, 18.6 grams of solution) and demineralized water (711 grams). The reactor phase was placed under $N_2$ atmosphere and heated to 82° C. A mixture of demineralized water (112 grams), sodium lauryl sulphate (30% solids in water, 37.2 grams of solution), methyl methacrylate (209.3 grams), n-butyl acrylate (453.56 grams) and methacrylic acid (34.88 grams) was placed in a large feeding funnel and emulsified with an overhead stirrer (monomer feed). Ammonium persulphate (1.75 grams) was dissolved in demineralized water (89.61 grams) and placed in a small feeding funnel (initiator feed). Ammonium persulphate (1.75 grams) was dissolved in demineralized water (10.5 grams), and this solution was added to the reactor phase. Immediately afterwards, 5% by volume of the monomer feed was added to the reactor phase. The reaction mixture then exothermed to 85° C. and was kept at 85° C. for 5 minutes. Then, the residual monomer feed and the initiator feed were fed to the reaction mixture over 90 minutes, maintaining a temperature of 85° C. After completion of the feeds, the monomer feed funnel was rinsed with demineralized water (18.9 grams) and reaction temperature maintained at 85° C. for 45 minutes. Subsequently, the mixture was cooled to room temperature and brought to pH=7.2 with ammonia solution (6.25 wt. % in demineralized water), and brought to 40% solids with further demineralized water.

EXAMPLE 1

A 2 L round bottom flask equipped with a condensor was placed under a $N_2$ atmosphere and charged with toluene (250 gram), propylene imine (325 gram), Bisphenol A-diglycidyl ether (387 gram) and $K_2CO_3$ (10.0 gram) and heated to 70° C. in 30 min, after which the mixture was stirred for 19 h at T=70° C. After filtration the excess of PI was removed in vacuo, followed by further purification via vacuum distillation, resulting in a whitish solid.

A 500 mL round bottom flask equipped with a thermometer and overhead stirrer was placed under a $N_2$ atmosphere and charged with the Bisphenol A-PI intermediate prepared as described above (42.72 gram), n-butanol (27.86 gram), m-tetramethylxylylene diisocyanate (91.83 gram) and 50.00 grams of acetone. The resulting mixture was heated to 60° C., after which bismuth neodecanoate (0.02 gram) was added. The mixture was kept at 60° C. using a water bath during exotherm, followed by stirring for 2 hours at 60° C. Samples were taken at regular intervals and the reaction progress was monitored using a Bruker Alpha FT-IR spectrometer until no change in NCO-stretch at 2200-2300 cm$^{-1}$ was observed. Subsequently, 37.59 grams of Voranol™ P-400 was added to the reaction mixture. The reaction mixture was then further reacted to complete disappearance of aforementioned NCO-stretch peak, and then 25.00 grams of acetone were added to dilute the reaction mixture. Finally, solvent was evaporated to yield a highly viscous yellowish liquid.

The calculated molecular weights of the theoretical main components was 1090.67 Da (no PPG chain) and 1817.14 Da (one PPG chain with 9 PO units); chemical structures are shown below.

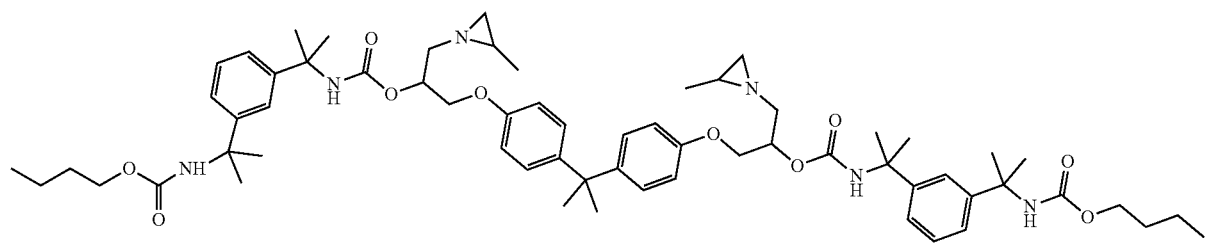 [SMILES: CCCCOC(=O)NC(C)(C)c1cccc(C(C)(C)NC(=O)OC(COc2ccc(C(C)(C)c3ccc(OCC(CN4CC4C)OC(=O)NC(C)(C)c4cccc(C(C)(C)NC(=O)OCCCC)c4)cc3)cc2)CN2CC2C)c1]

Molecular weight was confirmed by Maldi-TOF-MS: Calcd. [M+Na+]=1113.16 Da; Obs. [M+Na+]=1113.60 Da.

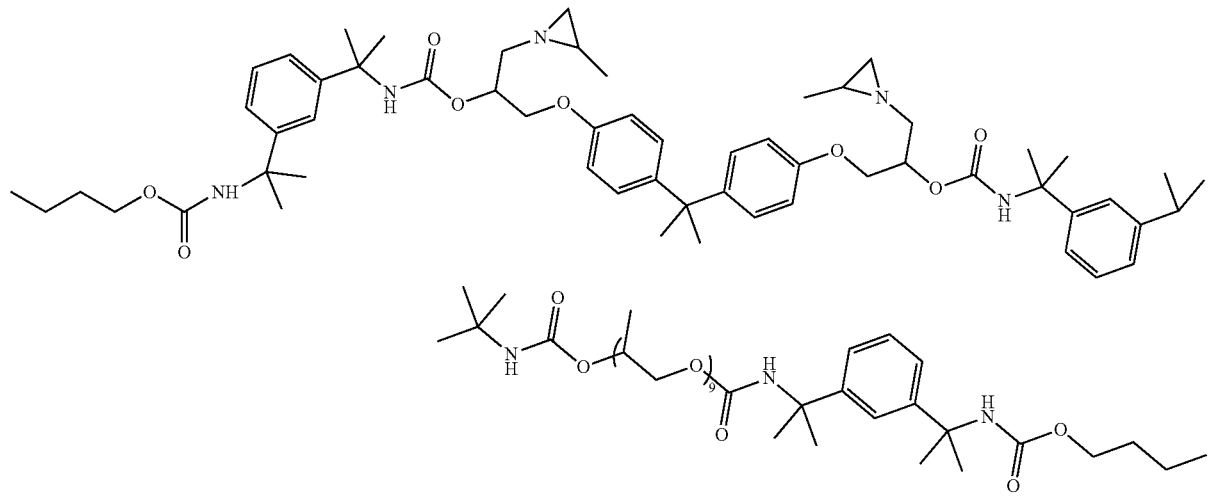

Molecular weight was confirmed by Maldi-TOF-MS: Calcd. [M+Na+]=1840.13 Da; Obs. [M+Na+]=1840.08 Da.

The following components with a mass below 580 Da were determined by LC-MS and quantified:

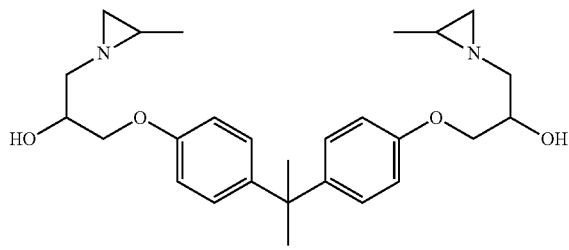 [SMILES: CC1CN1CC(O)COc1ccc(C(C)(C)c2ccc(OCC(O)CN3CC3C)cc2)cc1]

was present in the composition at less than 0.01 wt. %.

Genotoxicity Test

|  | Without S9 rat liver extract | | | | | | With S9 rat liver extract | | | | | |
| --- | --- | --- | --- | --- | --- | --- | --- | --- | --- | --- | --- | --- |
|  | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Composition 1 | 1.1 | 1.2 | 1.3 | 1.0 | 1.0 | 1.1 | 1.1 | 1.1 | 1.1 | 0.9 | 0.9 | 1.0 |

The genotoxicity test results show that the crosslinker composition of example 1 is non-genotoxic.

Performance of the synthesized compound as a crosslinker was assessed using spot tests on coating surfaces, based on procedures from the DIN 68861-1:2011-01 standard. For these tests, a solution of 1.1 parts of the viscous crosslinker liquid in 0.3 parts of acetone was added to 10.5 parts of P1 under continuous stirring, and the resulting mixture was further stirred for 30 minutes. Afterwards, this coating composition was filtered and applied to Leneta test cards using 100 μm wire rod applicators (Test 1-1). For reference, films were also cast from the same composition lacking a crosslinker (Blank 1-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

| Sample | 60 min | 240 min |
|---|---|---|
| Test 1-1 | 4 | 4 |
| Blank 1-2 | 1 | 1 |

Subsequently, 24 grams of the yellow liquid obtained as described above was mixed with 6.0 grams of methyl ethyl ketone (MEK) and 6.0 grams of acetone and incubated at 50° C. until a homogeneous solution was obtained. To this solution was added 0.03 grams of triethylamine (TEA) and then 2.4 grams of molten Maxemul™ 7101 dispersant. The resulting mixture was stirred for 5 minutes at room temperature using an IKA T25 Digital Ultra-Turrax® mixer with S 25 N-18 G head at 2,000 rpm. Then, stirring was increased to 10,000 rpm and 24 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements using a Brookfield DVE-LV viscometer (S62 spindle at 60 rpm unless mentioned otherwise). For these tests, the crosslinker dispersion was stored in an oven at 50° C. for 4 weeks. Every week, the viscosity and the particle size of the crosslinker dispersion were determined. Additionally, every week, 2.8 grams of the aged crosslinker dispersion was mixed with 10.5 grams of Polymer P1 under continuous stirring, and the resulting mixture was further stirred for 30 minutes. This coating composition was filtered and applied to Leneta test cards using 100 μm wire rod applicators (Test 1). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 1 (nm) | 319 | 321 | 325 | 293 | 292 |
| Viscosity 1 (mPa · s) | 86 | 72 | 86 | 60 | 60 |
| Test 1 | 3 | 3 | 3 | 3 | 3 |
| Test Blank | 1 | 1 | 1 | 1 | 1 |

EXAMPLE 2

A 2 L round bottom flask equipped with a condenser was placed under a $N_2$ atmosphere and charged with toluene (250 gram), propylene imine (330 gram), neopentyl-glycol-diglycidyl-ether ether (275 gram) and $K_2CO_3$ (10.0 gram) and heated to 70° C. in 30 min, after which the mixture was stirred for 22 h at T=70° C. After filtration the excess of PI was removed in vacuo, followed by further purification via vacuum distillation, resulting in a viscous solid.

A 500 mL round bottom flask equipped with a thermometer and overhead stirrer was placed under a $N_2$ atmosphere and charged with the NPG-PI intermediate from the first step (32.93 gram), n-butanol (14.77 gram), Desmodur W (52.29 gram) and 25.00 grams of acetone. The resulting mixture was heated to 50° C., after which bismuth neodecanoate (0.02 gram) was added. The mixture was allowed to exotherm to 60° C. followed by stirring for 90 minutes, after which another 25.00 grams of acetone and the reaction was continued for another 2 hours. Then, another 25.00 grams of acetone and 4.00 grams of n-butanol were added and reaction was continued. Samples were taken at regular intervals and the reaction progress was monitored using a Bruker Alpha FT-IR spectrometer, continuing reaction until the NCO-stretch at 2200-2300 $cm^{-1}$ had completely disappeared. Finally, solvent was evaporated to yield a colorless solid. The calculated molecular weights of the theoretical main component was 1002.73 Da, chemical structures are shown below.

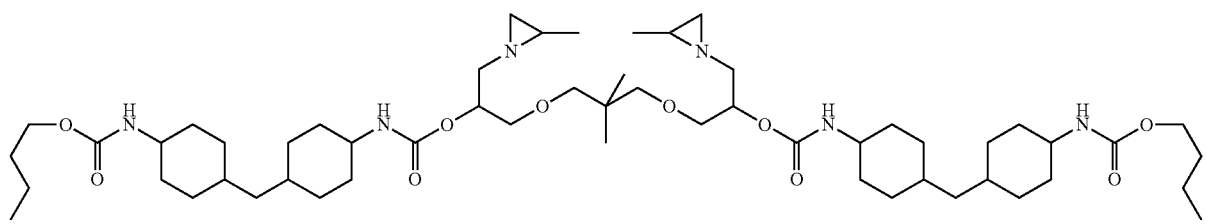 [SMILES: CCCCOC(=O)NC1CCC(CC2CCC(NC(=O)OC(COCC(C)(C)COCC(CN3CC3C)OC(=O)NC3CCC(CC4CCC(NC(=O)OCCCC)CC4)CC3)CN3CC3C)CC2)CC1]

Molecular weight was confirmed by Maldi-TOF-MS: Calcd. [M+Na+]=1025.72 Da; Obs. [M+Na+]=1025.67 Da.

The following components with a mass below 580 Da were determined by LC-MS and quantified:

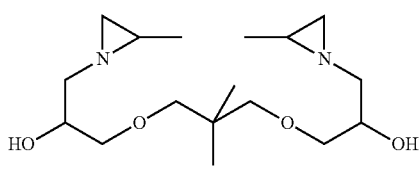 [SMILES: CC1CN1CC(O)COCC(C)(C)COCC(O)CN1CC1C]

was present in the composition at less than 0.01 wt. %.

Genotoxicity Test

|  | Without S9 rat liver extract | | | | | | With S9 rat liver extract | | | | | |
|---|---|---|---|---|---|---|---|---|---|---|---|---|
|  | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Composition 2 | 1.0 | 1.1 | 1.2 | 1.1 | 1.1 | 1.4 | 1.1 | 1.1 | 1.2 | 1.1 | 1.2 | 1.1 |

The genotoxicity test results show that the crosslinker composition of example 2 is non-genotoxic.

Performance of the synthesized compound as a crosslinker was assessed using spot tests on coating surfaces, based on procedures from the DIN 68861-1:2011-01 standard. For these tests, a solution of 0.5 parts of the solid crosslinker in 0.3 parts of acetone was added to 10.5 parts of P1 under continuous stirring, and the resulting mixture was further stirred for 30 minutes. Afterwards, this coating composition was filtered and applied to Leneta test cards using 100 μm wire rod applicators (Test 2-1). For reference, films were also cast from the same composition lacking a crosslinker (Blank 2-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

| Sample | 60 min | 240 min |
|---|---|---|
| Test 2-1 | 3 | 3 |
| Blank 2-2 | 1 | 1 |

For further performance tests, a solution of 1.0 parts of the solid crosslinker in 0.5 parts of acetone was added to 10.5 parts of A1 under continuous stirring, and the resulting mixture was further stirred for 30 minutes. Afterwards, this coating composition was filtered and applied to Leneta test cards using 100 μm wire rod applicators (Test 2-3). For reference, films were also cast from the same composition lacking a crosslinker (Blank 2-4). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

| Sample | 60 min | 240 min |
|---|---|---|
| Test 2-3 | 3 | 3 |
| Blank 2-4 | 1 | 1 |

EXAMPLE 3

A 500 mL round bottom flask equipped with a thermometer and overhead stirrer was placed under a $N_2$ atmosphere and charged with the Bisphenol A-PI intermediate prepared as described in Example 1 (21.25 gram), Ymer™ N-120 (23.01 gram), hexamethylene diisocyanate (31.45 gram) and 25.00 grams of acetone. The resulting mixture was heated to 60° C., after which bismuth neodecanoate (0.02 gram) was added. The mixture was kept at 50° C. using a water bath during exotherm. After 5 minutes, 18.73 grams of cyclohexanol was added to the mixture, again keeping the mixture at 50° C. using a water bath, followed by stirring for 2 hours at 50° C. Samples were taken at regular intervals and the reaction progress was monitored using a Bruker Alpha FT-IR spectrometer until no change in NCO-stretch at 2200-2300 $cm^{-1}$ was observed. Subsequently, 5.56 grams of Jeffamine D-230 was added to the reaction mixture. The reaction mixture was then further reacted to complete disappearance of aforementioned NCO-stretch peak. Then, the mixture was cooled to 40° C. and 170 grams of demineralized water was added gradually, yielding a bluish dispersion. The acetone was then removed from the dispersion using a rotary evaporator, and finally the pH of the dispersion was set to 11 using triethylamine.

The calculated molecular weights of the theoretical main components was 990.64 Da (no Jeffamine D-230 and no Ymer), 1406.93 Da (no Ymer, 3 PO groups in Jeffamine D-230), 2143.34 Da (no Jeffamine, 19 EO groups in Ymer), 2515.61 Da (3 PO groups in Jeffamine D-230, 18 EO groups in Ymer); chemical structures are shown below.

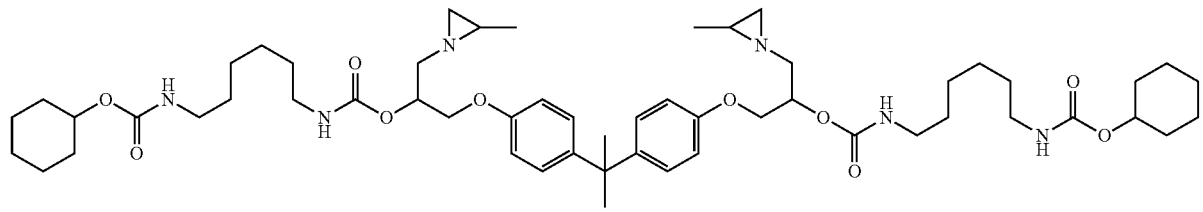 [SMILES: CC1CN1CC(COc1ccc(C(C)(C)c2ccc(OCC(CN3CC3C)OC(=O)NCCCCCCNC(=O)OC3CCCCC3)cc2)cc1)OC(=O)NCCCCCCNC(=O)OC1CCCCC1]

Molecular weight was confirmed by Maldi-TOF-MS:
Calcd. [M+Na+]=1013.63 Da; Obs. [M+Na+]=1013.68 Da.
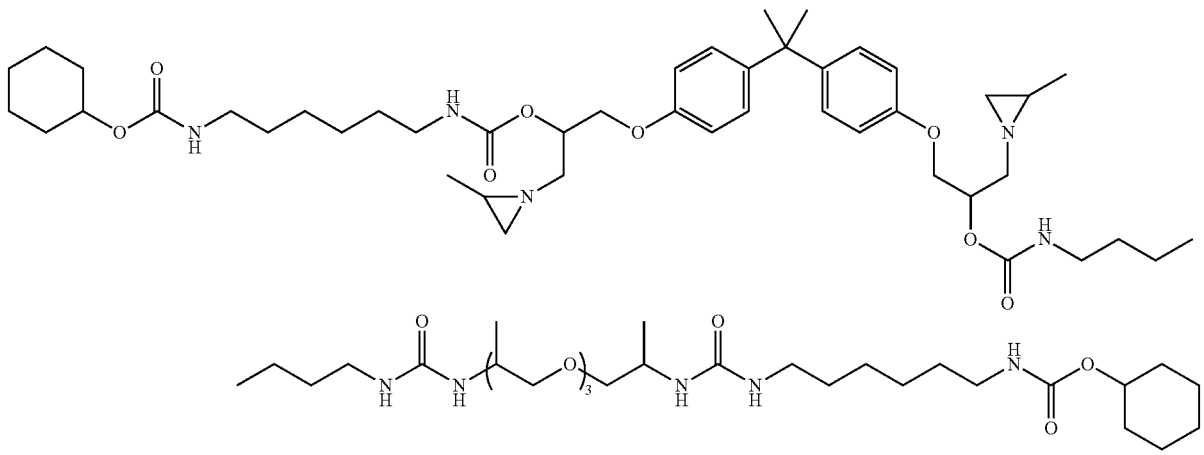
Molecular weight was confirmed by Maldi-TOF-MS:
Calcd. [M+Na+]=1429.93 Da; Obs. [M+Na+]=1430.01 Da.
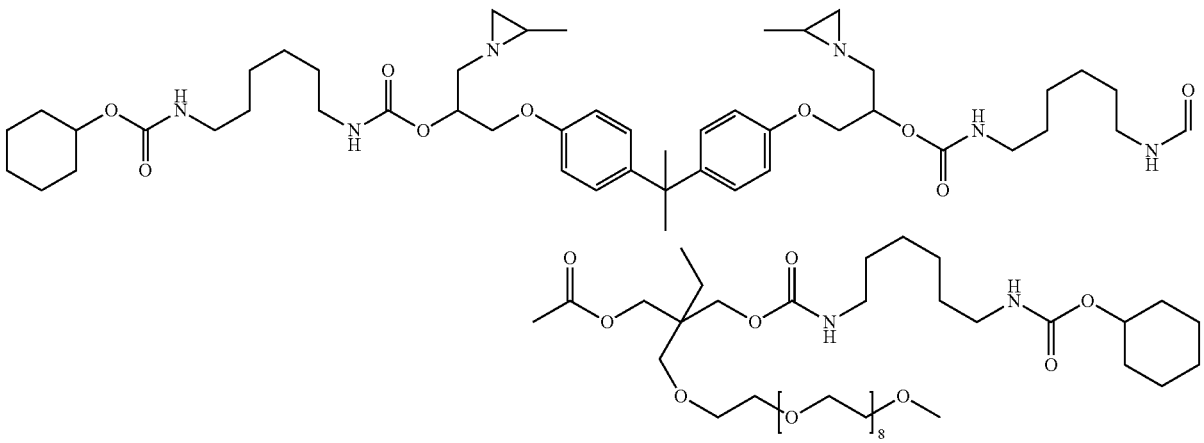
45
Molecular weight was confirmed by Maldi-TOF-MS:
Calcd. [M+Na+]=2166.33 Da; Obs. [M+Na+]=2166.47 Da.
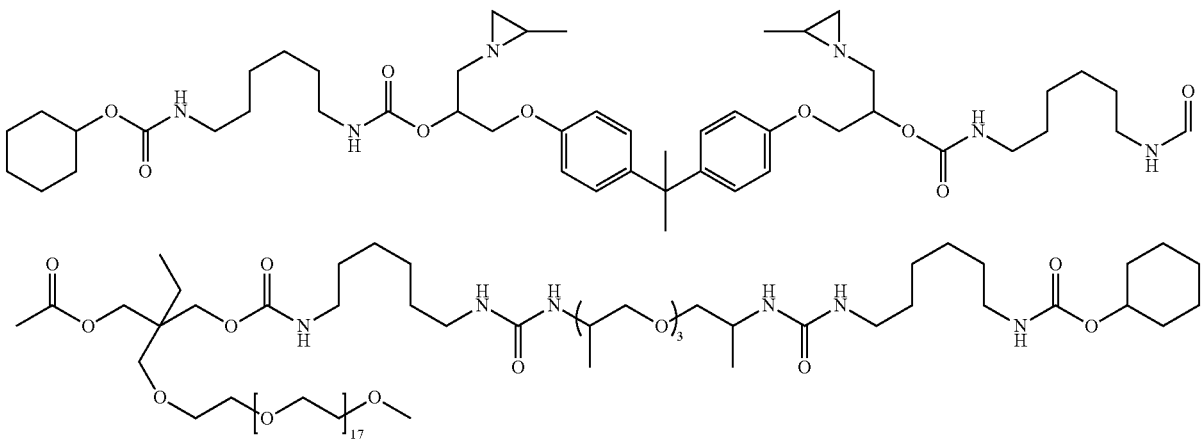

Molecular weight was confirmed by Maldi-TOF-MS: Calcd. [M+Na+]=2538.60 Da; Obs. [M+Na+]=2538.76 Da.

The following components with a mass below 580 Da were determined by LC-MS and quantified:

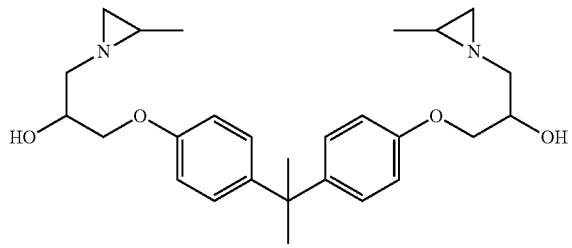 [SMILES: CC1CN1CC(O)COc1ccc(C(C)(C)c2ccc(OCC(O)CN3CC3C)cc2)cc1]

was present in the composition at less than 0.01 wt. %.

Genotoxicity Test

|  | Without S9 rat liver extract | | | | | | With S9 rat liver extract | | | | | |
| --- | --- | --- | --- | --- | --- | --- | --- | --- | --- | --- | --- | --- |
|  | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Composition 3 | 1.1 | 1.1 | 1.3 | 1.0 | 1.1 | 1.0 | 1.2 | 1.3 | 1.5 | 1.0 | 1.1 | 1.0 |

The genotoxicity test results show that the crosslinker composition of example 3 is non genotoxic.

Performance of the synthesized compound as a crosslinker was assessed using spot tests on coating surfaces, based on procedures from the DIN 68861-1:2011-01 standard. For these tests, 2.9 parts of crosslinker dispersion was added to 10.5 parts of P1 under continuous stirring, and the resulting mixture was further stirred for 30 minutes. Afterwards, this coating composition was filtered and applied to Leneta test cards using 100 μm wire rod applicators (Test 3-1). For reference, films were also cast from the same composition lacking a crosslinker (Blank 3-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

| Sample | 60 min | 240 min |
| --- | --- | --- |
| Test 3-1 | 3 | 3 |
| Blank 3-2 | 1 | 1 |

For further performance tests, 5.9 parts of the crosslinker dispersion was added to 10.5 parts of A1 under continuous stirring, and the resulting mixture was further stirred for 30 minutes. Afterwards, this coating composition was filtered and applied to Leneta test cards using 100 μm wire rod applicators (Test 3-3). For reference, films were also cast from the same composition lacking a crosslinker (Blank 3-4). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

| Sample | 60 min | 240 min |
| --- | --- | --- |
| Test 3-3 | 3 | 3 |
| Blank 3-4 | 1 | 1 |

Functional performance and stability of the crosslinker dispersion were assessed using spot tests on coating surfaces, based on procedures from the DIN 68861-1 standard, and viscosity measurements using a Brookfield DVE-LV viscometer (S62 spindle at 60 rpm unless mentioned otherwise). For these tests, 100 grams of crosslinker dispersion obtained as described above and diluted with 170 grams of demineralized water, was stored in an oven at 50° C. for 4 weeks. Every week, the viscosity of the aged diluted crosslinker dispersion was determined. Additionally, every week, 2.9 grams of the aged diluted crosslinker dispersion was mixed with 10.5 grams of Polymer P1 under continuous stirring, and the resulting mixture was further stirred for 30 minutes. This coating composition was filtered and applied to Leneta test cards using 100 μm wire rod applicators (Test 3). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
| --- | --- | --- | --- | --- | --- |
| Particle size 3 (nm) | 253 | 209 | 227 | 216 | 192 |
| Viscosity 3 (mPa · s) | 86 | 74 | 56 | 60 | 66 |
| Test 3 | 3 | 3 | 3 | 3 | 3 |
| Test Blank | 1 | 1 | 1 | 1 | 1 |

EXAMPLE 4

A 500 mL round bottom flask equipped with a thermometer and overhead stirrer was placed under a $N_2$ atmosphere and charged with the Bisphenol A-PI intermediate prepared as described in Example 1 (15.92 gram), Ymer™ N-120 (13.37 gram), isophorone diisocyanate (31.13 gram), Oxymer™ M112 (21.91 gram), and 25.00 grams of acetone. The resulting mixture was heated to 60° C., after which bismuth neodecanoate (0.02 gram) was added. The mixture was kept at 50° C. using a water bath during exotherm. The mixture was stirred for 165 minutes at 50° C. Samples were taken at regular intervals and the reaction progress was monitored using a Bruker Alpha FT-IR spectrometer until no change in NCO-stretch at 2200-2300 cm$^{-1}$ was observed. Subsequently, 9.16 grams of n-methylbutylamine was added to the reaction mixture, the mixture was stirred for another 5 minutes, and then 8.52 grams of 3-cyclohexylamino-1-propanesulfonic acid sodium salt was added. The reaction mixture was then further reacted to complete disappearance of aforementioned NCO-stretch peak. Then, 42 grams of acetone was added and the mixture was cooled to 40° C. Subsequently, 180 grams of demineralized water was added gradually, yielding a blueish dispersion. The acetone was then removed from the dispersion using a rotary evaporator, and finally the pH of the dispersion was set to 11 using triethylamine.

The resulting material had the following generalized structure:

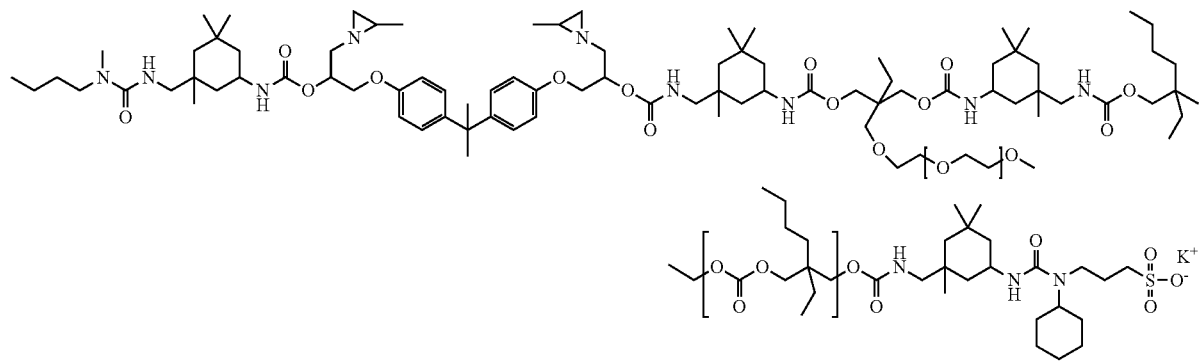

25

The calculated molecular weights of the theoretical main components and their chemical structures are shown below:

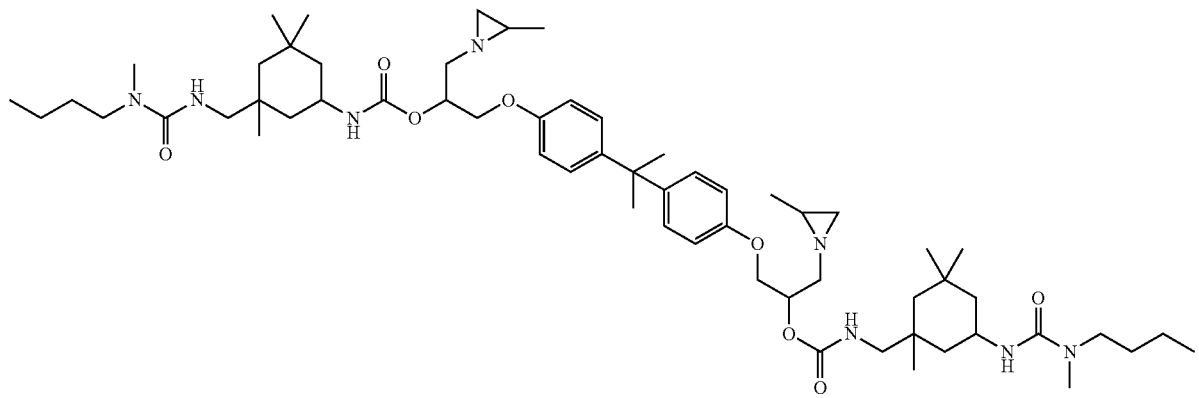 [SMILES: CCCCN(C)C(=O)NCC1(C)CC(NC(=O)OC(COc2ccc(C(C)(C)c3ccc(OCC(CN4CC4C)OC(=O)NCC4(C)CC(NC(=O)N(C)CCCC)CC(C)(C)C4)cc3)cc2)CN2CC2C)CC(C)(C)C1]

45

Molecular weight was confirmed by Maldi-TOF-MS: Calcd. [M+Na+]=1095.76 Da; Obs. [M+Na+]=1095.79 Da.

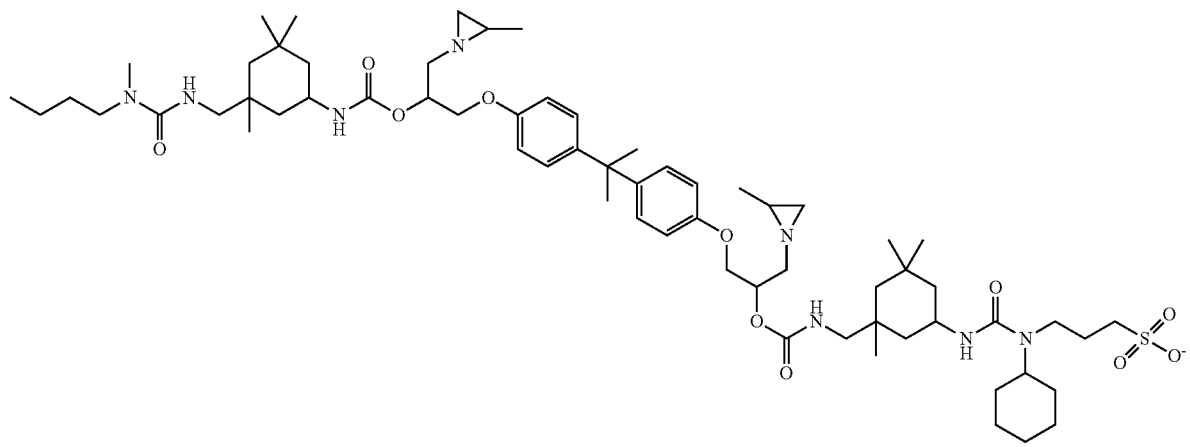 [SMILES: CCCCN(C)C(=O)NCC1(C)CC(NC(=O)OC(COc2ccc(C(C)(C)c3ccc(OCC(CN4CC4C)OC(=O)NCC4(C)CC(NC(=O)N(CCCS(=O)(=O)[O-])C5CCCCC5)CC(C)(C)C4)cc3)cc2)CN2CC2C)CC(C)(C)C1]

Molecular weight was confirmed by Maldi-TOF-MS: Calcd. [M+2*Na+]=1251.74 Da; Obs. [M+2*Na+]=1251.76 Da.

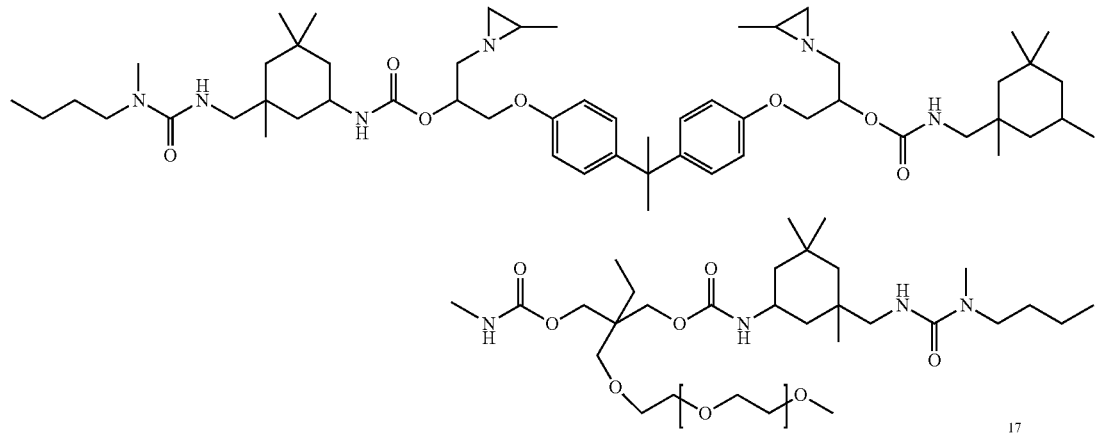

Molecular weight was confirmed by Maldi-TOF-MS: Calcd. [M+Na+]=2258.48 Da; Obs. [M+Na+]=2258.61 Da.

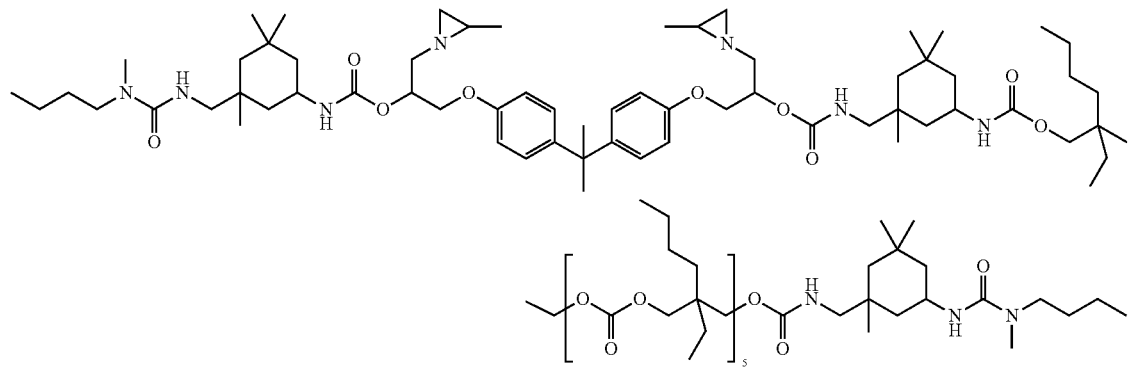

Molecular weight was confirmed by Maldi-TOF-MS: Calcd. [M+Na+]=2408.67 Da; Obs. [M+Na+]=2408.79 Da.

The following components with a mass below 580 Da were determined by LC-MS and quantified:

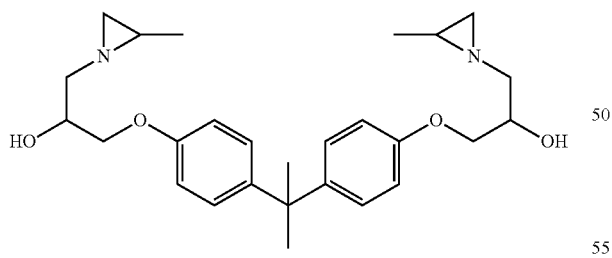

was present in the composition at less than 0.01 wt. %.

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Composition 4 | 1.1 | 1.2 | 1.5 | 0.9 | 0.8 | 0.7 | 1.1 | 1.3 | 1.6 | 0.9 | 0.9 | 0.8 |

Genotoxicity Test

The genotoxicity test results show that the crosslinker composition of example 4 only has weakly positive induced genotoxicity.

Performance of the synthesized compound as a crosslinker was assessed using spot tests on coating surfaces, based on procedures from the DIN 68861-1:2011-01 standard. For these tests, 4.2 parts of crosslinker dispersion was added to 10.5 parts of P1 under continuous stirring, and the resulting mixture was further stirred for 30 minutes. Afterwards, this coating composition was filtered and applied to Leneta test cards using 100 µm wire rod applicators (Test 4-1). For reference, films were also cast from the same composition lacking a crosslinker (Blank 4-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

| Sample | 60 min | 240 min |
| --- | --- | --- |
| Test 4-1 | 3 | 3 |
| Blank 4-2 | 1 | 1 |

For further performance tests, 8.5 parts of the crosslinker dispersion was added to 10.5 parts of A1 under continuous stirring, and the resulting mixture was further stirred for 30 minutes. Afterwards, this coating composition was filtered and applied to Leneta test cards using 100 µm wire rod applicators (Test 4-3). For reference, films were also cast from the same composition lacking a crosslinker (Blank 4-4). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

| Sample | 60 min | 240 min |
| --- | --- | --- |
| Test 4-3 | 3 | 3 |
| Blank 4-4 | 1 | 1 |

Functional performance and stability of the crosslinker dispersion were assessed using spot tests on coating surfaces, based on procedures from the DIN 68861-1 standard, and viscosity measurements using a Brookfield DVE-LV viscometer (S62 spindle at 60 rpm unless mentioned otherwise). For these tests, 100 grams of crosslinker dispersion obtained as described above and diluted with 194 grams of demineralized water, was stored in an oven at 50° C. for 4 weeks. Every week, the viscosity of the aged diluted crosslinker dispersion was determined. Additionally, every week, 4.2 grams of the aged diluted crosslinker dispersion was mixed with 10.5 grams of Polymer P1 under continuous stirring, and the resulting mixture was further stirred for 30 minutes. This coating composition was filtered and applied to Leneta test cards using 100 µm wire rod applicators (Test 4). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
| --- | --- | --- | --- | --- | --- |
| Particle size 4 (nm) | 85 | 82 | 80 | 81 | 104 |
| Viscosity 4 (mPa · s) | 18 | 18 | 28 | 48 | 176 |
| Test 4 | 3 | 3 | 3 | 3 | 3 |
| Test Blank | 1 | 1 | 1 | 1 | 1 |

EXAMPLE 5

Crosslinker was synthesized as Example 1.

Subsequently, 32 grams of the yellow liquid obtained as described above was mixed with 8.0 grams of methyl ethyl ketone (MEK) and 8.0 grams of acetone and incubated at 50° C. until a homogeneous solution was obtained. To this solution was added 2.4 grams of molten Maxemul™ 7101 dispersant. The resulting mixture was stirred for 5 minutes at room temperature using an IKA T25 Digital Ultra-Turrax® mixer with S 25 N-18 G head at 2,000 rpm. Then, stirring was increased to 10,000 rpm and 32 grams of demineralized water, brought to pH 12.5 using 15% aqueous potassium hydroxide solution, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 12.5 with 15% aqueous potassium hydroxide solution.

Functional performance and stability of the crosslinker dispersion were assessed using spot tests on coating surfaces, based on procedures from the DIN 68861-1 standard, and viscosity measurements using a Brookfield DVE-LV viscometer (S62 spindle at 60 rpm unless mentioned otherwise). For these tests, the crosslinker dispersion was stored in an oven at 50° C. for 4 weeks. Every week, the viscosity and the particle size of the crosslinker dispersion were determined. Additionally, every week, 2.8 grams of the aged crosslinker dispersion was mixed with 10.5 grams of Polymer P1 under continuous stirring, and the resulting mixture was further stirred for 30 minutes. This coating composition was filtered and applied to Leneta test cards using 100 µm wire rod applicators (Test 5). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
|---|---|---|---|---|---|
| Particle size 5 (nm) | 275 | 269 | 291 | 290 | 299 |
| Viscosity 5 (mPa·s) | 61 | 49 | 48 | 55 | 56 |
| Test 5 | 3 | 3 | 3 | 3 | 3 |
| Test Blank | 1 | 1 | 1 | 1 | 1 |

EXAMPLE 6

A 500 mL round bottom flask equipped with a thermometer and overhead stirrer was placed under a $N_2$ atmosphere and charged with the Bisphenol A-PI intermediate prepared as described in Example 1 (17.13 gram), 1-butoxy-3-(2-methylaziridin-1-yl)propan-2-ol intermediate prepared as described in WO 2020/020714 A1 (28.24 gram), Desmodur W (39.55 gram) and 25.00 grams of acetone. The resulting mixture was heated to 60° C., after which bismuth neodecanoate (0.02 gram) was added. The mixture was kept at 60° C. using a water bath throughout the exothermic reaction, followed by stirring for 2 hours at 60° C. Samples were taken at regular intervals and the reaction progress was monitored using a Bruker Alpha FT-IR spectrometer until no change in NCO-stretch at 2200-2300 $cm^{-1}$ was observed. Subsequently, 15.08 grams of Voranol™ P-400 was added to the reaction mixture. The reaction mixture was then further reacted to complete disappearance of aforementioned NCO-stretch peak. Finally, 20.00 grams of acetone were added to yield a light yellow solution. The calculated molecular weights of the theoretical main components and their chemical structures are shown below:

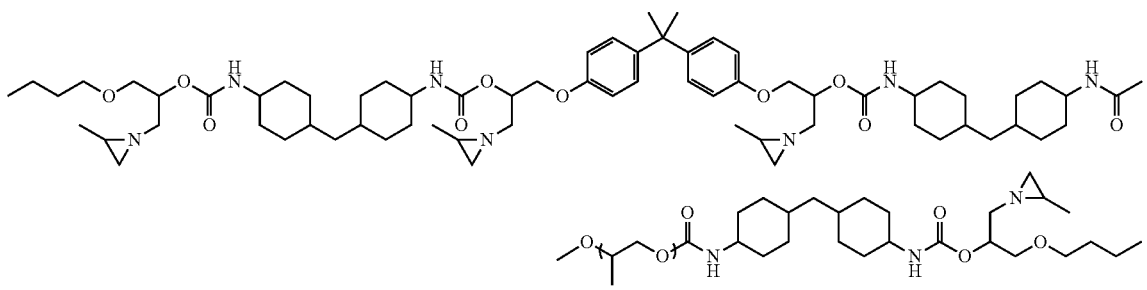

Molecular weight was confirmed by Maldi-TOF-MS: Calcd. [M+Na+]=2062.40 Da; Obs. [M+Na+]=2062.39 Da.

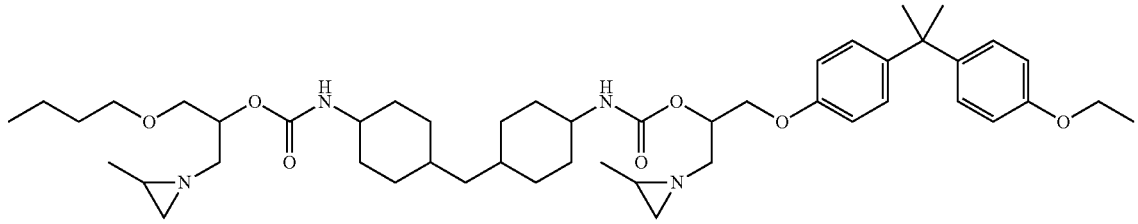

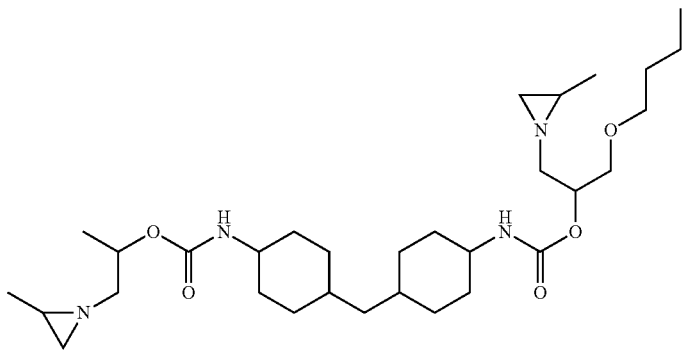

Molecular weight was confirmed by Maldi-TOF-MS: Calcd. [M+Na+]=1375.92 Da; Obs. [M+Na+]=1375.86 Da.

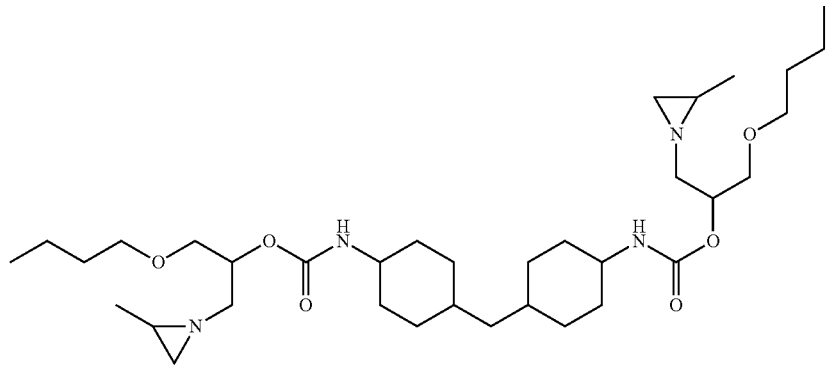 [SMILES: CCCCOCC(CN1CC1C)OC(=O)NC1CCC(CC2CCC(NC(=O)OC(COCCCC)CN3CC3C)CC2)CC1]

Molecular weight was confirmed by Maldi-TOF-MS: Calcd. [M+Na+]=659.47 Da; Obs. [M+Na+]=659.41 Da.

The following components with a mass below 580 Da were determined by LC-MS and quantified:

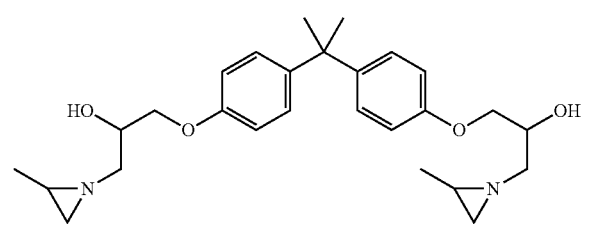 [SMILES: CC1CN1CC(O)COc1ccc(C(C)(C)c2ccc(OCC(O)CN3CC3C)cc2)cc1]

was present in the composition at less than 0.01 wt. % and

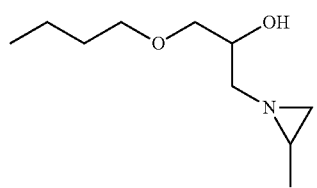

was present at less than 0.01 wt. %.

Genotoxicity Test

|  | Without S9 rat liver extract | | | | | | With S9 rat liver extract | | | | | |
| --- | --- | --- | --- | --- | --- | --- | --- | --- | --- | --- | --- | --- |
|  | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Composition 6 | 1.2 | 1.3 | 1.6 | 1.2 | 1.2 | 1.3 | 1.4 | 1.6 | 1.8 | 1.2 | 1.3 | 1.6 |

The genotoxicity test results show that the crosslinker composition of example 6 only has weakly positive induced genotoxicity.

Performance of the synthesized compound as a crosslinker was assessed using spot tests on coating surfaces, based on procedures from the DIN 68861-1:2011-01 standard. For these tests, a solution of 1.3 parts of the viscous crosslinker liquid in 0.4 parts of acetone was added to 10.5 parts of P1 under continuous stirring, and the resulting mixture was further stirred for 30 minutes. Afterwards, this coating composition was filtered and applied to Leneta test cards using 100 µm wire rod applicators (Test 6-1). For reference, films were also cast from the same composition lacking a crosslinker (Blank 6-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

| Sample | 60 min | 240 min |
| --- | --- | --- |
| Test 6-1 | 3 | 3 |
| Blank 6-2 | 1 | 1 |

Subsequently, 15 grams of the yellow solution obtained in the previous step was mixed with 1.5 grams of methyl ethyl ketone (MEK) and incubated at 50° C. until a homogeneous solution was obtained. To this solution was added 0.03 grams of triethylamine (TEA) and then 1.1 grams of Atlas™ G-5002L-LQ dispersant. The resulting mixture was stirred for 5 minutes at room temperature using an IKA T25 Digital Ultra-Turrax® mixer with S 25 N-18G head at 2,000 rpm. Then, stirring was increased to 10,000 rpm and 10.4 grams of demineralized water, brought to pH 11 using triethylamine, was added gradually to the mixture over 15 minutes. During this addition process, the mixer was moved around the reaction vessel continuously. After completion of the addition, the resulting dispersion was stirred at 5,000 rpm for 10 more minutes, and the pH of the dispersion was set to 11 with TEA.

Functional performance and stability of the crosslinker dispersion were assessed using spot tests on coating surfaces, based on procedures from the DIN 68861-1 standard, and viscosity measurements as well as particle size measurements. For these tests, the crosslinker dispersion was stored in an oven at 50° C. for 4 weeks. Every week, the viscosity and the particle size of the crosslinker dispersion were determined. Additionally, every week, 1.2 grams of the aged crosslinker dispersion was mixed with 10.5 grams of Polymer P1 under continuous stirring, and the resulting mixture was further stirred for 30 minutes. This coating composition was filtered and applied to Leneta test cards using 100 μm wire rod applicators (Test 6). For reference, films were also cast from the same composition lacking the crosslinker dispersion (Test Blank). The films were dried for 1 hour at 25° C., then annealed at 50° C. for 16 hours. Subsequently, a piece of cotton wool was soaked in 1:1 EtOH:demineralized water and placed on the film for 1 hour. After removal of the EtOH and 60 minutes recovery, the following results were obtained (a score of 1 indicates complete degradation of the film, 5 indicates no damage visible):

Performance and Stability Test

| Sample | Week 0 | Week 1 | Week 2 | Week 3 | Week 4 |
| --- | --- | --- | --- | --- | --- |
| Particle size 6 (nm) | 206 | 200 | 199 | 202 | 215 |
| Viscosity 6 (mPa · s) | 178 | 230 | 205 | 231 | 288 |
| Test 6 | 3 | 3 | 3 | 3 | 3 |
| Test Blank | 1 | 1 | 1 | 1 | 1 |

The invention claimed is:

1. A multi-aziridine compound having:
   a) at least 2 of the following structural units (A):

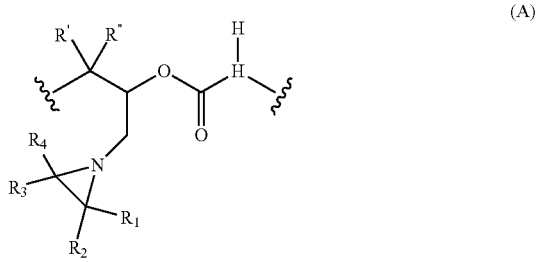

(A)

whereby
R$_1$ is H;
R$_2$ and R$_4$ are independently chosen from H, a linear group containing from 1 to 8 carbon atoms and optionally containing one or more heteroatoms, a branched or cyclic group containing from 3 to 8 carbon atoms and optionally containing one or more heteroatoms, phenyl, benzyl, or pyridinyl;
R$_3$ is chosen from a linear group containing from 1 to 8 carbon atoms and optionally containing one or more heteroatoms, a branched or cyclic group containing from 3 to 8 carbon atoms and optionally containing one or more heteroatoms, phenyl, benzyl, or pyridinyl;
or R$_2$ and R$_3$ (in case R$_2$ is different than H) may be part of the same cyclic group containing from 3 to 8 carbon atoms;
R' and R" are independently H or an aliphatic hydrocarbon group containing from 1 to 12 carbon atoms; and
   b) a molecular weight of from 600 to 20000 Daltons, wherein the molecular weight is determined using MALDI-TOF mass spectrometry; and the multi-aziridine compound is obtained by reacting at least a polyisocyanate and a compound (B) with the following structural formula:

whereby n is an integer equal to or larger than 2, Z is an n-valent radical or a mixture of n-valent radicals and D has the following structural formula:

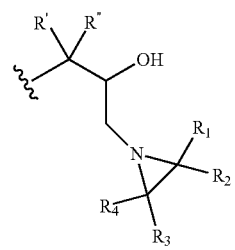

whereby the molar ratio of moiety D to isocyanate moieties on polyisocyanates is from 0.5 to 2.

2. The multi-aziridine compound according to claim 1, wherein R$_2$ is H, R$_3$ is CH$_3$ and R$_4$ is H.

3. The multi-aziridine compound according to claim 1, wherein R' and R" are H.

4. The multi-aziridine compound according to claim 1, wherein the multi-aziridine compound contains 2 to 10 structural units (A).

5. The multi-aziridine compound according to claim 1, wherein the multi-aziridine compound has a molecular weight of at least 800 Daltons and at most 10000 Daltons.

6. The multi-aziridine compound according to claim 1, wherein the polyisocyanate is a polyisocyanate with aliphatic reactivity in which all of the isocyanate groups are directly bonded to aliphatic or cycloaliphatic hydrocarbon groups, irrespective of whether aromatic hydrocarbon groups are also present.

7. The multi-aziridine compound according to claim 1, wherein the polyisocyanate is a diisocyanate.

8. The multi-aziridine compound according to claim 1, wherein the Z is a divalent radical (n=2) and

is according to the following formula:

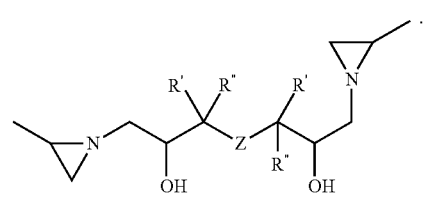

9. The multi-aziridine compound according to claim 7, wherein the diisocyanate is selected from the group consisting of 1,5-pentamethylene diisocyanate, 1,6-hexamethylene diisocyanate, isophorone diisocyanate, 4,4'-dicyclohexyl methane diisocyanate, 2,2,4-trimethyl hexamethylene diisocyanate, 2,4,4-trimethyl hexamethylene diisocyanate, tetramethylxylene diisocyanate (all isomers), and any mixture thereof.

10. The multi-aziridine compound according to claim 1, wherein compound (B) is obtained by reacting at least a n-functional polyepoxide compound with an aziridine with the following structural formula:

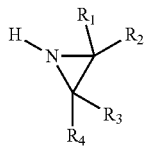

whereby $R_1$, $R_2$, $R_3$ and $R_4$ are defined as in any of the preceding claims.

11. The multi-aziridine compound according to claim 10, wherein the n-functional polyepoxide is a difunctional polyepoxide compound.

12. The multi-aziridine compound according to claim 10, wherein the n-functional polyepoxide is selected from the group consisting of bisphenol A diglycidyl ether, hydrogenated bisphenol A diglycidyl ether, neopentyl glycol diglycidyl ether, butanediol diglycidyl ether, ethylene glycol diglycidyl ether, 1,6-Hexanediol diglycidyl ether, polypropyleneglycol diglycidyl ether, poly(ethylene glycol) diglycidyl ether and any mixture thereof.

13. A crosslinker composition comprising at least one multi-aziridine compound according to claim 1 and further comprising at least one additional component.

14. The crosslinker composition according to claim 13, wherein the amount of aziridinyl group functional molecules having a molecular weight lower than 580 Daltons is lower than 5 wt. %, relative to the total weight of the crosslinker composition, whereby the molecular weight is determined using LC-MS.

15. The crosslinker composition according to claim 13, wherein the crosslinker composition is an aqueous dispersion comprising particles of the multi-aziridine compound.

16. The crosslinker composition according to claim 15, wherein the aqueous dispersion has a pH in the range from 9.5 to 11.5.

17. A two-component system comprising a first component and a second component each of which is separate and distinct from each other and wherein the first component comprises a carboxylic acid functional polymer dissolved and/or dispersed in an aqueous medium, whereby the carboxylic acid functional polymer contains carboxylic acid groups and/or carboxylate groups and the second component comprises the multi-aziridine compound according to claim 1.

18. An aqueous coating composition comprising dispersed particles X of the multi-aziridine compound according to claim 1, and carboxylic-acid functional polymer particles Y, whereby the carboxylic acid functional polymer contains carboxylic acid groups and/or carboxylate groups, and whereby the aqueous coating composition having a pH ranging from 8 to 14, with the proviso that particles X neither comprise carboxylic-acid functional polymer nor other compounds crosslinkable with the multi-aziridine compound as defined herein and particles Y neither comprise multi-aziridine compound nor other compounds crosslinkable with the carboxylic acid functionality of the carboxylic acid functional polymer.

19. The aqueous coating composition according to claim 18, wherein the carboxylic acid functional polymer has an acid value of from 2 to 135 mg KOH/gram of the carboxylic acid functional polymer.

20. The aqueous coating composition according to claim 18, wherein the aqueous coating composition is self-crosslinkable.

21. The aqueous coating composition according to claim 19, wherein the carboxylic acid functional polymer has an acid value of from 3 to 70 mg KOH/g carboxylic acid functional polymer.

22. A two-component system comprising a first component and a second component each of which is separate and distinct from each other and wherein the first component comprises a carboxylic acid functional polymer dissolved and/or dispersed in an aqueous medium, whereby the carboxylic acid functional polymer contains carboxylic acid groups and/or carboxylate groups and the second component comprises the crosslinker composition according to claim 13.

* * * * *